United States Patent
Zhang et al.

(10) Patent No.: US 9,956,152 B2
(45) Date of Patent: May 1, 2018

(54) SKIN-PROTECTION COMPOSITION CONTAINING DENDROBIUM-BASED INGREDIENTS

(71) Applicant: Hong Kong Baptist University, Kowloon (HK)

(72) Inventors: Hongjie Zhang, Kowloon (HK); Siu Wai Tsang, Kowloon (HK); Yu Zhu, Kowloon (HK)

( * ) Notice: Subject to any disclaimer, the term of this patent is extended or adjusted under 35 U.S.C. 154(b) by 0 days. days.

(21) Appl. No.: 15/352,903

(22) Filed: Nov. 16, 2016

(65) Prior Publication Data
US 2017/0057906 A1 Mar. 2, 2017

Related U.S. Application Data

(63) Continuation-in-part of application No. 14/740,410, filed on Jun. 16, 2015, now Pat. No. 9,526,706, and a continuation-in-part of application No. 15/531,636, filed on Nov. 15, 2016, now Pat. No. 9,738,581, which is a continuation-in-part of application No. 14/740,410.

(51) Int. Cl.
| | |
|---|---|
| *C07C 69/80* | (2006.01) |
| *C07C 43/205* | (2006.01) |
| *C07C 43/215* | (2006.01) |
| *C07C 69/34* | (2006.01) |
| *A61K 8/34* | (2006.01) |
| *A61K 8/37* | (2006.01) |
| *A61K 8/33* | (2006.01) |
| *A61Q 19/02* | (2006.01) |
| *A61Q 17/04* | (2006.01) |
| *C07C 39/21* | (2006.01) |
| *C07C 69/736* | (2006.01) |
| *C07C 69/753* | (2006.01) |
| *A61K 31/09* | (2006.01) |
| *C07C 39/15* | (2006.01) |

(52) U.S. Cl.
CPC ............... *A61K 8/347* (2013.01); *A61K 8/33* (2013.01); *A61K 8/37* (2013.01); *A61K 31/09* (2013.01); *A61Q 17/04* (2013.01); *A61Q 19/02* (2013.01); *C07C 39/15* (2013.01); *C07C 39/21* (2013.01); *C07C 43/2055* (2013.01); *C07C 43/215* (2013.01); *C07C 69/34* (2013.01); *C07C 69/736* (2013.01); *C07C 69/753* (2013.01); *C07C 2101/08* (2013.01)

(58) Field of Classification Search
CPC ....... C07C 69/80; C07C 37/003; C07C 39/15; C07C 39/21; C07C 43/2055; C07C 43/215; C07C 69/34; C07C 69/736; C07C 69/753; C07C 2101/08; A61K 8/33; A61K 8/347; A61K 8/37; A61K 31/09; A61Q 17/04; A61Q 19/02
USPC ......................................................... 514/721
See application file for complete search history.

(56) References Cited

FOREIGN PATENT DOCUMENTS

| CN | 102369223 A | 3/2012 | |
| CN | 102816090 A | * 12/2012 | ............. C07C 69/80 |

OTHER PUBLICATIONS

Lu et al., Influence of Glucuronidation and Reduction Modifications of Resveratrol on its Biological Activities, ChemBioChem, 2013, 14, 1094-1104.
L.R. Sklar et al., "Effects of ultraviolet radiation, visible light, and infrared radiation on erythema and pigmentation: a review," Photochem. Photobiol. Sci., 2013, 12, pp. 54-64.
Y. Mishima et al., "Selective Aberration and Pigment Loss in Melanosomes of Malignant Melanoma Cells in Vitro by Glycosylation Inhibitors: Premelanosomes as Glycoprotein," The Journal of investigative dermatology, 1983, 81, pp. 106-114.
Maresca et al., "Skin phototype: a new perspective," Pigment Cell Melanoma Res., 2015, pp. 1-12.
S. Del Bino et al., "Variations in skin colour and the biological consequences of ultraviolet radiation exposure" by British Journal of Dermatology (2013) 169 (Suppl. 3), pp. 33-40.
International Search Report of PCT/CN2017/107798 dated Jan. 26, 2018.
Venera Cardile et al, Chemo-enzymatic synthesis and cell-growth inhibition activity of resveratrol analogues, Bioorganic Chemistry, Feb. 28, 2005, No. 1 vol. 33, p. 22-33.
Diana C. Rueda et la, Identification of dihydrostilbenes in Pholidota chinensis as a new scaffold for GABAA receptor modulators, Bioorganic & Medicinal Chemistry, Feb. 15. 2014, No. 4 vol. 22, p. 1276-1284.

* cited by examiner

*Primary Examiner* — Kristin A Vajda
(74) *Attorney, Agent, or Firm* — Idea Intellectual Limited; Margaret A. Burke; Sam T. Yip

(57) ABSTRACT

A skin-protection composition is shown that comprises stilbenoid(s) and/or stilbenoid-containing extract(s) obtained from *Dendrobium* plants, such as *Dendrobium officinale* and *Dendrobium nobile* for the management of melanogenesis, skin-darkening and skin-aging. More particularly, the usage of *Dendrobium* ingredients and stilbenoids is shown to reduce the formation of melanin in melanocytes. The usage of *Dendrobium* ingredients and stilbenoids is also shown to reduce the generation of reactive oxygen species and oxidative free radicals. The use of *Dendrobium*-derived extracts or ingredients or stilbenoids is shown in the formulation of skin-protection, skin-whitening and/or anti-skin aging products.

3 Claims, 20 Drawing Sheets

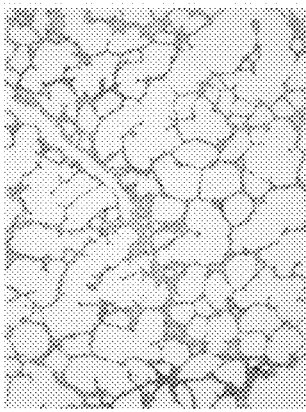
Figure 3A Control
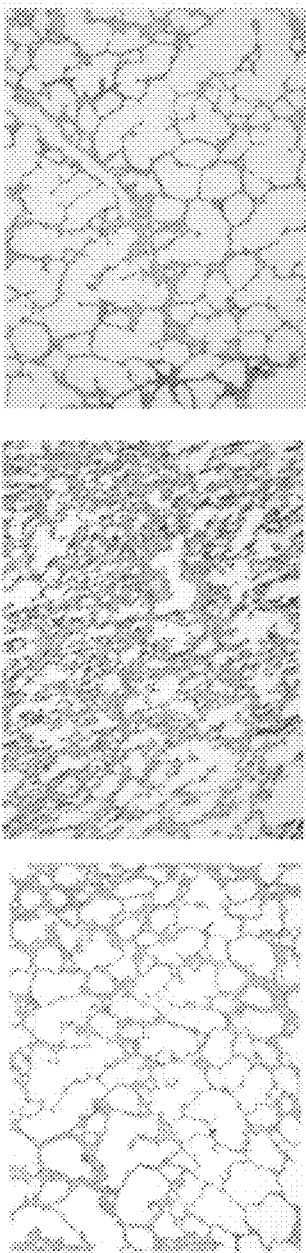
Figure 3B Cerulein
Figure 3C Cerulein + D-Res 10mg
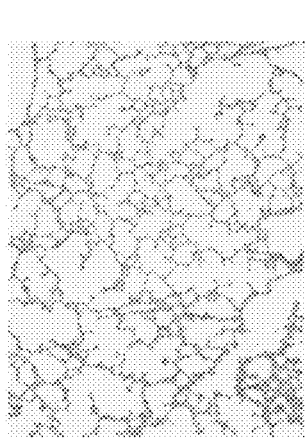
Figure 3E Cerulein + D-Res 50mg
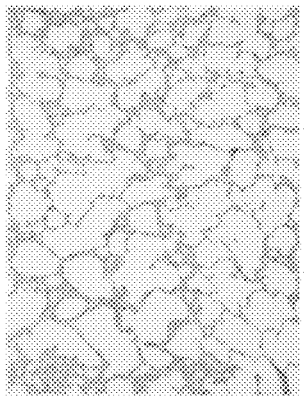
Figure 3D Cerulein + D-Res 20mg

SKIN-PROTECTION COMPOSITION CONTAINING DENDROBIUM-BASED INGREDIENTS

CROSS-REFERENCE TO RELATED APPLICATIONS

The present application is a continuation-in-part of application Ser. No. 14/740,410 filed on Jun. 16, 2015 and is also a continuation-in-part of application Ser. No. 15/351,636 filed on Nov. 15, 2016, which is itself a continuation-in-part of application Ser. No. 14/740,410 filed on Jun. 16, 2015, the disclosure of each of which is hereby incorporated by reference in its entirety.

FIELD OF INVENTION

The present invention relates to a skin-protection composition that comprises stilbenoid(s) and/or stilbenoid-containing extract(s) isolated from *Dendrobium* plants, such as *Dendrobium officinale* and *Dendrobium nobile* for the management of melanogenesis, skin-darkening and skin-aging. More particularly, it relates to the usage of *Dendrobium* ingredients to reduce the formation of melanin in melanocytes. It also relates to the usage of *Dendrobium* ingredients to reduce the generation of reactive oxygen species and oxidative free radicals. This invention relates to the use of *Dendrobium*-derived extracts or ingredients in the formulation of skin-protection, skin-whitening and/or anti-skin aging products.

BACKGROUND OF INVENTION

In general, light skin can become darker upon exposure to sunlight, which is the primary source of ultraviolet (UV) radiation in our daily life. Upon UV exposure, reactive oxygen species (ROS) and highly volatile free radicals are provoked. Consequently, our skin gets darkened since melanin-producing cells, or melanocytes, located in the skin's epidermis are prone to produce more melanin in order to minimize the indirect damages of body cells [Sklar L R, Almutawa F, Lim H W, Hamzavi I. Effects of ultraviolet radiation, visible light, and infrared radiation on erythema and pigmentation: a review. *Photochemical & Photobiological Sciences* 2013; 12:54-64]. In other words, the elevation of melanin production is actually a defense mechanism against UV radiation; however, the accumulation of melanin may result in deleterious biological effects, including abnormal pigmentation, skin darkening as well as aesthetic problems, e.g. freckles or chloasmata [Mishima Y, Imokawa G. Selective aberration and pigment loss in melanosomes of malignant melanoma cells in vitro by glycosylation inhibitors: premelanosomes as glycoprotein. *Journal of Investigative Dermatology* 1983; 81: 106-114]. In this regard, the formation of ROS and free radicals plays a pivotal mechanism leading to skin-darkening and skin-aging. Scavenging of ROS and free radicals can definitely protect skin cells from the oxidative damages. Currently, topical antioxidants, e.g. vitamin A, vitamin C, vitamin E, ascorbic acid (AC), butylated hydroxyanisole (BHA) and/or their derivatives, have been widely used in over-the-counter skincare products. However, these products are not effective skin-protection agents possessing both depigmentation and antioxidant properties. To this end, their effectiveness on skin protection is highly limited and restrained. There is a conception in the general public that dark and dull skin makes people look old, depressing and disfigured; therefore, people, especially in oriental countries, are eager to maintain a fair complexion and a pleasing appearance of their integumentary system.

In fact, melanin refers to a group of endogenous pigments that give multitude of skin colors, i.e. from the basic skin tone to freckles, birth marks, age spots, also in eyes and hair. In the human body, melanins are produced by melanocytes and classified into three major types: eumelanin, pheomelanin and neuromelanin. They differ in chemical structures and physical properties, and thus they are elicited upon different biological responses against external stimuli. Eumelanin and pheomelanin are the two types of melanin that can be found in the skin. Eumelanin provides primarily dark brown to black colors whereas pheomelanin produces reddish colors [Maresca V, Flori E, Picardo M. Skin phototype: a new perspective. *Pigment Cell & Melanoma Research* 2015; 28:378-389]. In melanogenesis, tyrosinase is the major rate-limiting enzyme for regulating melanin production in epidermal melanocytes whereas tyrosinase-related proteins (TRPs) are melanogenic enzymes that control the proportion of carboxylated subunits in melanin biopolymers. When exposed to sunlight, melanin deposition is accelerated as more alpha-melanocyte-stimulating hormone ($\alpha$-MSH) is released from melanocytes. In addition to the overt skin darkening, such acceleration is indeed a defense mechanism against the UV-induced generation of ROS and/or free radicals, which consequently causes most of the wrinkles, freckles, rashes and age spots on the face. Collectively, the harmful effects of constant or excessive sunlight or UV exposure include skin aging, skin damage and even skin cancer. The present invention provides a composition that efficiently attenuates the biosynthesis of melanin as well as oxidative substances. By any means of mechanism, the present invention is able to restrain melanin accumulation and/or oxidative damage in the skin, hence skin protection can be achieved.

The composition of present invention comprises stilbenoids and/or extracts obtained from plants of the genus *Dendrobium* (Orchidaceae family, commonly called "Shi Hu"), particularly from the species *D. officinale* and *D. nobile*. The said stilbenoids, explicitly trans-resveratrol and dihydro-resveratrol, and extracts can be formulated into a cosmetic blend of skin-protection, skin-whitening and/or anti-skin aging products for human skin as they are found to attenuate the generation of ROS and oxidative free radicals, and/or reduce cellular melanin content in melanocytes. The reduction of melanin formation may be associated with an inhibition of the activity of pigment-producing enzymes, namely tyrosinase, TRP-1 and TRP2.

SUMMARY OF INVENTION

Accordingly, the objective of this invention relates to a skin-protection composition that comprises stilbenoid(s) and/or stilbenoid-containing extract(s) isolated from *Dendrobium* plants, such as *Dendrobium officinale* and *Dendrobium nobile*. This invention also relates to the use of *Dendrobium*-derived extracts or ingredients in reducing melanin formation in melanocytes for the management of melanogenesis and skin-darkening. Particularly, this invention also relates to the use of *Dendrobium*-derived extracts or ingredients in the formulation of skin-protection, skin-whitening and/or anti-skin aging products.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1),

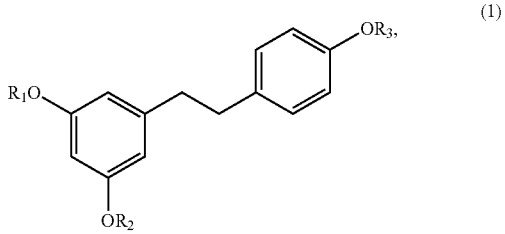

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

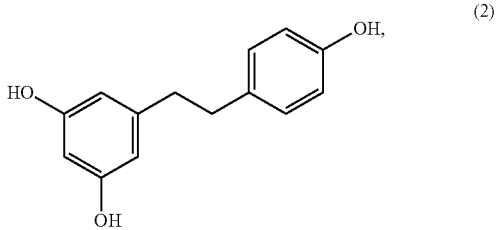 [SMILES: Oc1ccc(CCc2cc(O)cc(O)c2)cc1]

and the derivatives or chemical variants thereof or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and the associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2),

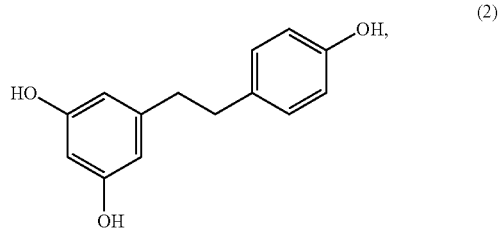

which is a stilbenoid derivative having a chemical name of trans-3,5,4'-trihydroxybibenzyl by hydrogenating of trans-resveratrol.

In a second embodiment of the second aspect of the present invention there is provided a method of preparing the compound of molecular formula $C_{14}H_{14}O_3$ and of formula (2) wherein the hydrogenating of trans-resveratrol comprises steps of stirring a solution of trans-resveratrol in anhydrous ethanol (EtOH) at room temperature under 5 atm $H_2$ pressure in the presence of 10% Pd/C for 8 hours;
filtering off the catalyst from the stirred solution;
evaporating the filtrate in vacuum to produce a residue;
eluting the residue using silica gel chromatographic separation with petroleum ether and ethyl acetate (1:1) to produce dihydro-resveratrol.

In a first embodiment of the third aspect of the present invention, there is provided a compound for suppressing a fibrotic mediator of stellate cells present in an internal organ of a subject in need with a formula of

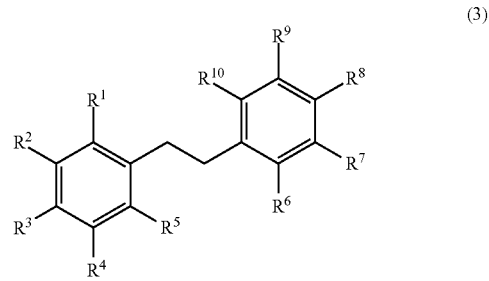

wherein
$R^2$ and $R^4$ are each independently selected from —$OR^{11}$ and —$OC(O)R^{11}$;
$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof, or a mixture of said compound, the derivative and/or chemical variants thereof.

In a second embodiment of the third aspect of the present invention there is provided a compound for suppressing a fibrotic mediator of stellate cells present in an internal organ of a subject in need with a formula of (i)

(ii)

(iii)

(iv)

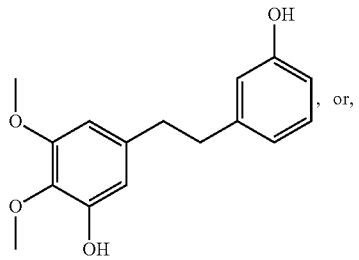
(v)

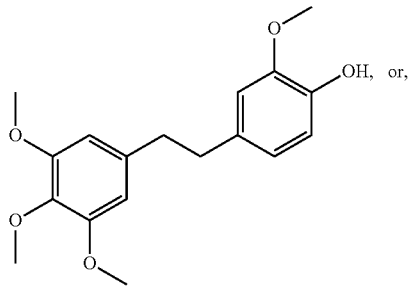
(vi)

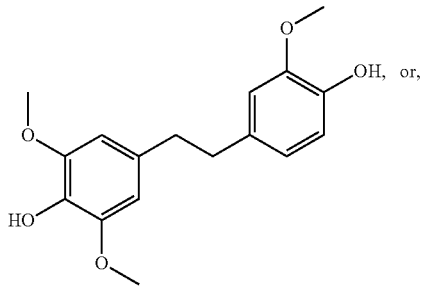
(vii)

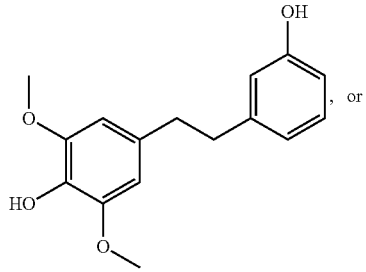
(viii)

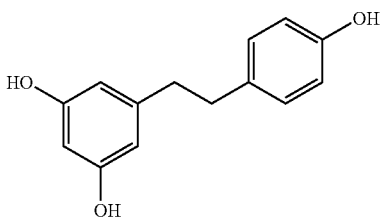
(2)

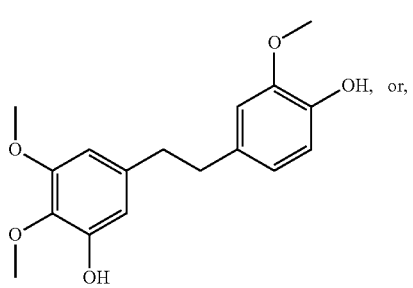

In a first embodiment of the fourth aspect of the present invention there is provided a method for suppressing fibrotic mediator(s) in stellate cells present in an internal organ of a subject in need by using a composition comprising compounds i to viii or dihydro-resveratrol.

In a second embodiment of the fourth aspect of the present invention there is provided a method for suppressing fibrotic mediator(s) in stellate cells present in an internal organ of a subject in need wherein the composition is administered to a subject in need thereof with a dosage of at least 1.622 mg/kg/day wherein said composition is consisted of a compound with a formula of

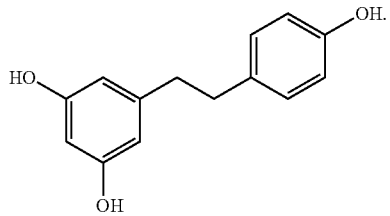

(2)

In a third embodiment of the fourth aspect of the present invention there is provided a method for suppressing fibrotic mediator(s) in stellate cells present in an internal organ of a subject in need wherein the said subject is human.

In a fourth embodiment of the fourth aspect of the present invention there is provided a method for suppressing fibrotic mediator(s) in stellate cells present in an internal organ of a subject in need wherein the composition is administered orally to said subject in need thereof.

In a fifth embodiment of the fourth aspect of the present invention there is provided a method for suppressing fibrotic mediator(s) in stellate cells present in an internal organ of a subject in need wherein the internal organ comprises pancreas, liver, kidney and lung.

In a first embodiment of the fifth aspect of the present invention there is provided a compound for treating pancreatogenic diabetes (or Type 3c diabetes milieus) in a subject in need with a therapeutically effective amount of a formula of

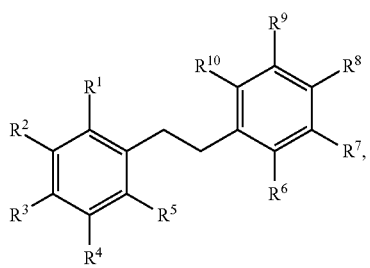

(3)

wherein
$R^2$ and $R^4$ are each independently selected from —$OR^{11}$ and —$OC(O)R^{11}$;
$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;
$R^{11}$ is independently hydrogen or selected from hydrocarbyl and heterocyclyl, either of which is optionally substituted with 1, 2, 3, 4 or 5 $R^{12}$;
$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;
$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
or an enantiomer thereof;
or a pharmaceutically acceptable salt or prodrug thereof,
or a mixture of said compound, the derivative and/or chemical variants thereof.

In a second embodiment of the fifth aspect of the present invention there is provided a method for treating pancreatogenic diabetes (or Type 3c diabetes milieus) in a subject in need by using a composition comprising compounds of a formula of

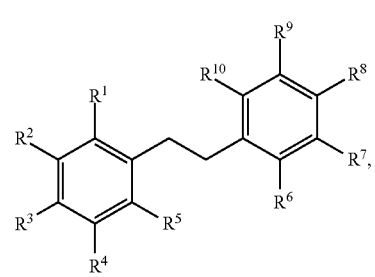

(3)

wherein
$R^2$ and $R^4$ are each independently selected from —$OR^{11}$ and —$OC(O)R^{11}$;
$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;
$R^{11}$ is independently hydrogen or selected from hydrocarbyl and heterocyclyl, either of which is optionally substituted with 1, 2, 3, 4 or 5 $R^{12}$;
$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;
$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
or an enantiomer thereof;
or a pharmaceutically acceptable salt or prodrug thereof,
or a mixture of said compound, the derivative and/or chemical variants thereof.

In a third embodiment of the fifth aspect of the present invention there is provided a method for treating pancreatogenic diabetes (or Type 3c diabetes milieus) in a subject in need wherein the composition is administered to a subject in need thereof with a dosage of at least 1.622 mg/kg/day wherein said composition is consist of a compound with a formula of

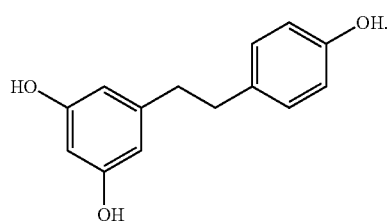

(2)

In a fourth embodiment of the fifth aspect of the present invention there is provided a method for treating pancreatogenic diabetes (or Type 3c diabetes milieus) in a subject in need wherein the said subject is human.

In a fifth embodiment of the fifth aspect of the present invention there is provided a method for treating pancreatogenic diabetes (or Type 3c diabetes milieus) in a subject in need wherein the composition is administered orally to said subject in need thereof.

In a first embodiment of the sixth aspect of the present invention there is provided a compound for treating pancreatogenic diabetes (or Type 3c diabetes milieus) in a subject in need with a therapeutically effective amount of a formula of

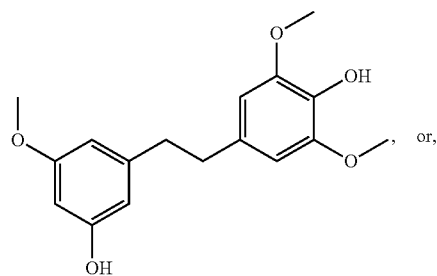
(i)

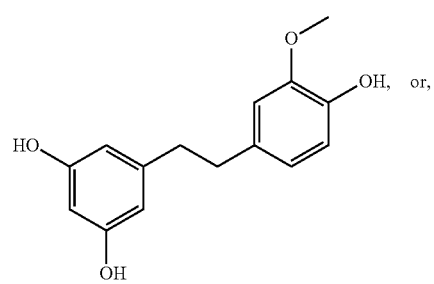
(ii)

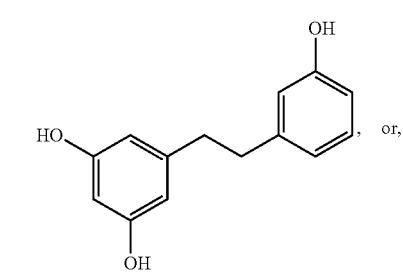
(iii)

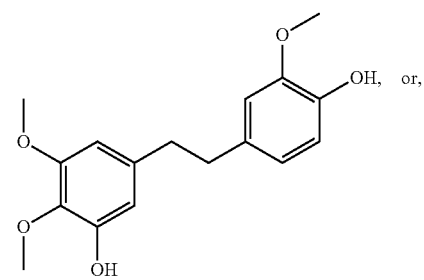
(iv)

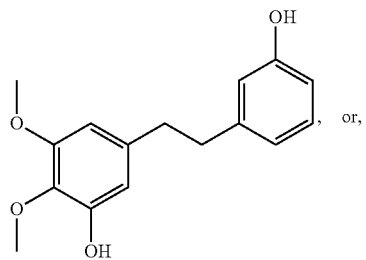
(v)

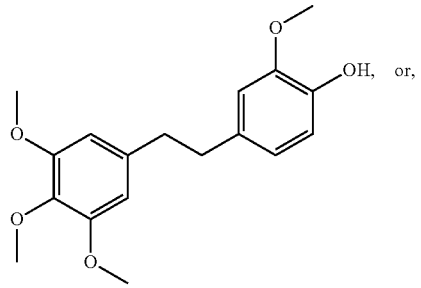
(vi)

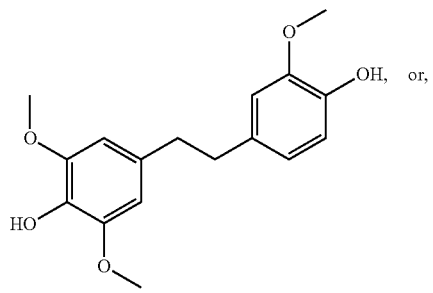
(vii)

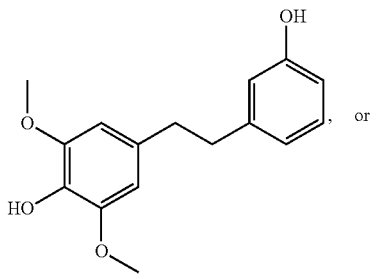
(viii)

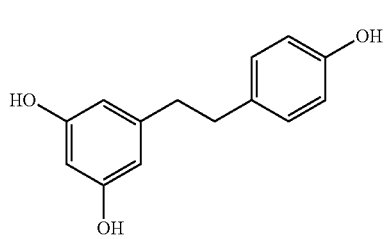
(2)

In a second embodiment of the sixth aspect of the present invention there is provided a method for treating pancreatogenic diabetes (or Type 3c diabetes milieus) in a subject wherein the composition is administered to a subject in need thereof with a dosage of at least 1.622 mg/kg/day wherein said composition is consist of a compound with a formula of

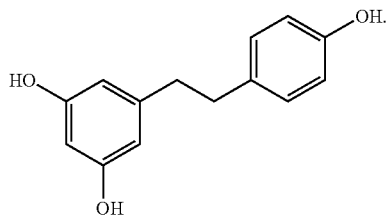
(2)

In a third embodiment of the sixth aspect of the present invention there is provided a method for treating pancreatogenic diabetes (or Type 3c diabetes milieus) in a subject wherein the said subject is human.

In a first embodiment of the fifth aspect of the present invention there is provided a compound comprising formula (4):

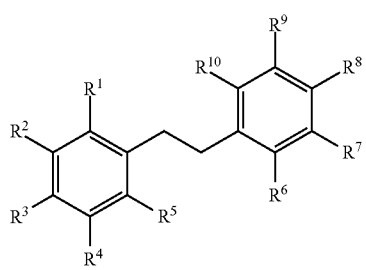
(4)

wherein
$R^2$, $R^4$, $R^8$ are each independently selected from —$OR^{11}$, —$OCH_2R^{12}$, —$OC(O)R^{11}$, —$OCH_2C(O)OR^{12}$ and —$OC(O)CH_2R^{12}$;

$R^1$, $R^3$, $R^5$, $R^6$, $R^7$, $R^9$ and $R^{10}$ are each independently selected from hydrogen, halogen, trifluoromethyl, —$OR^{12}$ and —$OC(O)R^{12}$; or $R^2$ and $R^3$, or $R^7$ and $R^8$ may be taken together with the carbon atoms to which they are attached to form a cyclic group;

$R^{11}$ is independently selected from —$(CH_2)$-hydrocarbyl, $C_{2-10}$ alkyl, alkenyl and heterocyclyl. Each of these groups is optionally substituted with 1, 2, 3, 4 or 5 $R^{13}$;

$R^{12}$ is independently selected from hydrocarbyl and heterocyclyl, either of which is optionally substituted with 1, 2, 3, 4 or 5 $R^{13}$;

$R^{13}$ is independently selected from halogen, trifluoromethyl, cyano, nitro, oxo, —$OR^{14}$, —$C(O)R^{15}$, —$C(O)N(R^{14})R^{15}$, —$C(O)OR^{14}$, —$OC(O)R^{15}$, —$S(O)_2R^{14}$, —$S(O)_2N(R^{14})R^{15}$, —$N(R^{14})R^{15}$;

$R^{14}$ and $R^{15}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;
or a pharmaceutically acceptable salt or prodrug thereof.

In a second embodiment of the fifth aspect of the present invention there is provided a compound of formula (4) wherein said compound is an optically pure stereoisomer, enantiomer, racemate or diastereomer.

In a third embodiment of the fifth aspect of the present invention there is provided a pharmaceutical composition comprising an effective amount of the compound of formula (4) and a pharmaceutically acceptable carrier thereof.

In a fourth embodiment of the fifth aspect of the present invention there is provided a pharmaceutical composition comprising an effective amount of the skin whitening and skin protection compound of formula (4) and a pharmaceutically acceptable carrier thereof.

In a fifth embodiment of the fifth aspect of the present invention there is provided a compound of formula (4) is selected from DR1, DR2, DR3, DR4, DR5, DR6, DR7, DR8, DR9, DR10 or DR11 with the following formulae respectively:

DR1

DR2
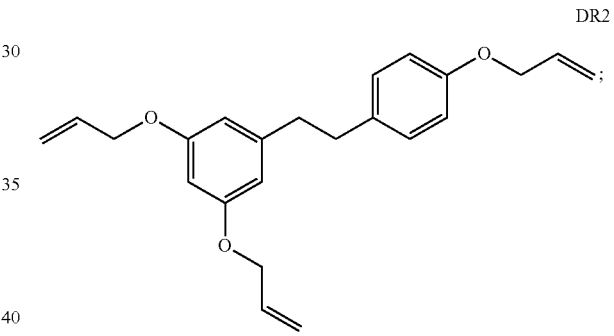

DR3
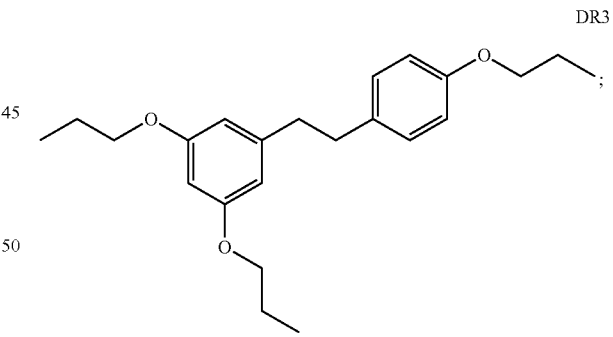

DR4
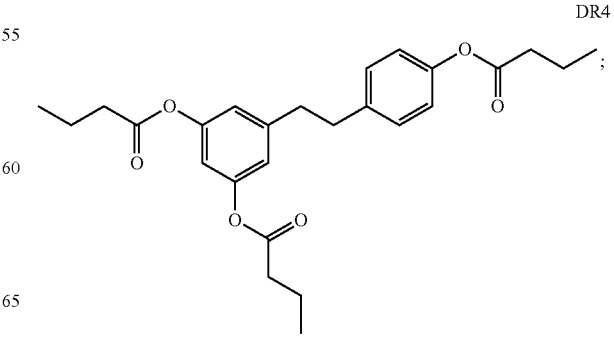

DR5
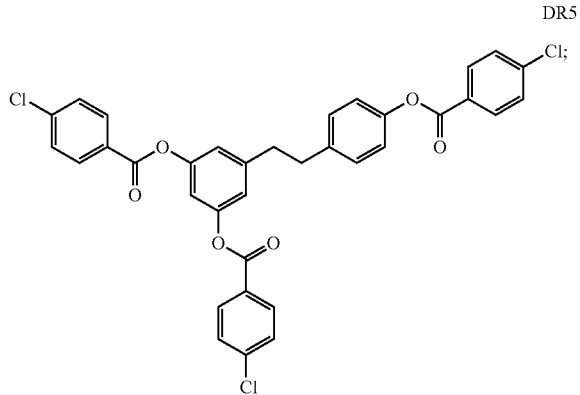

DR6
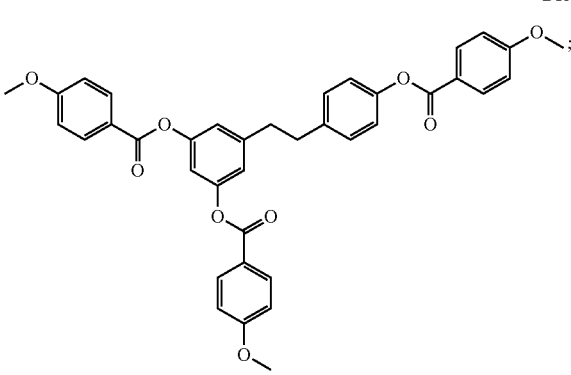

DR7
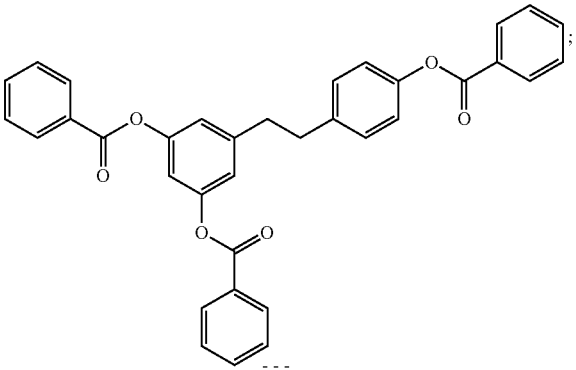

DR8
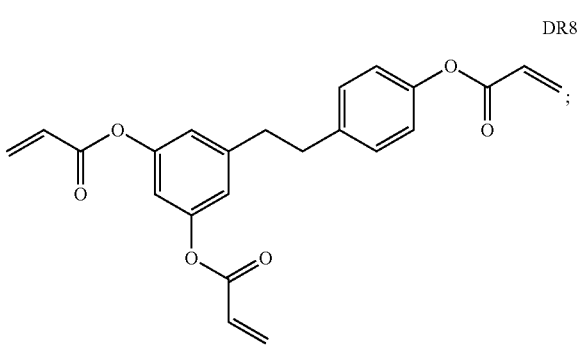

DR9
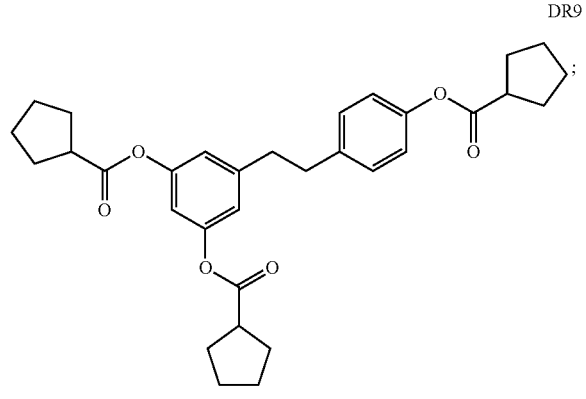

DR10
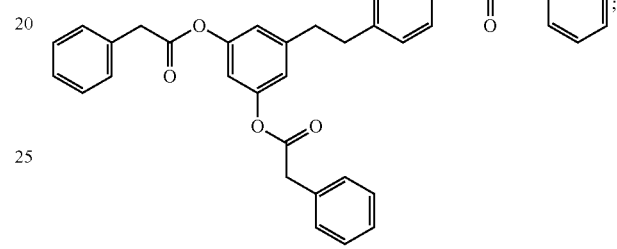

DR11
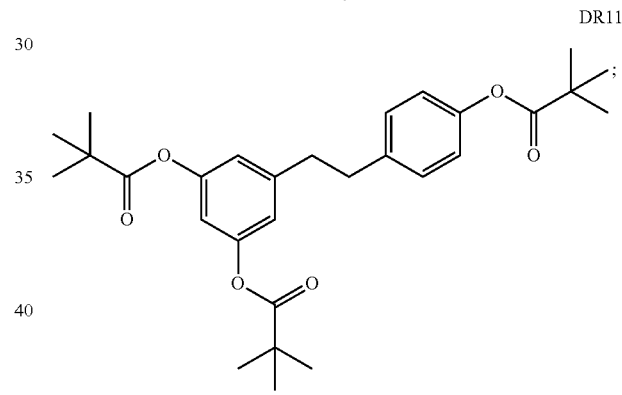

or a pharmaceutically acceptable salt or prodrug thereof.

In a sixth embodiment of the fifth aspect of the present invention there is provided a method of using the compound of formula (4) and/or the derivatives or chemical variants thereof and/or in combination with one or more other pharmaceutically acceptable skin-whitening and skin-protection agent(s) in treatment, prevention or delay of progression of a skin darkening in a subject in needs thereof.

In a seventh embodiment of the fifth aspect of the present invention there is provided the method of using the compound of formula (4) and/or the derivatives or chemical variants thereof and/or in combination with one or more other pharmaceutically acceptable skin-whitening and skin-protection agent(s) in treatment, prevention or delay of progression of a skin darkening, wherein said subject is a human.

In an eighth embodiment of the fifth aspect of the present invention there is provided a method of treating and preventing development and progression of a skin darkening comprising administering the compound of formula (4) to a subject in needs thereof.

In a ninth embodiment of the fifth aspect of the present invention there is provided a method of treating and preventing development and progression of a skin darkening comprising administering the compound of formula (4) to a subject in needs thereof wherein said subject is a human.

In a tenth embodiment of the fifth aspect of the present invention there is provided the method of using the compound of formula (4) and/or the derivatives or chemical variants thereof and/or in combination with one or more other pharmaceutically acceptable skin-whitening and skin-protection agent(s), wherein the compound is applied topically.

In a eleventh embodiment of the fifth aspect of the present invention there is provided the pharmaceutical composition, wherein the composition is in the form of a day cream, a night cream, a face lotion, a body lotion, a body butter, a skin peel, a mask, a shower gel, a sun cream, a sun lotion, an after sun cream or an after sun lotion.

In a first embodiment of the sixth aspect of the present invention there is provided a skin whitening and skin protection against UV exposure, skin damage and aging compound comprising formula (5):

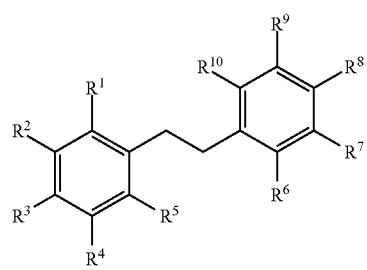

(5)

wherein $R^2$, $R^4$, $R^8$ are each independently selected from —$OR^{11}$, —$OCH_2R^{11}$, —$OC(O)R^{11}$, —$OCH_2C(O)OR^{11}$ and —$OC(O)CH_2R^{11}$;

$R^1$, $R^3$, $R^5$, $R^6$, $R^7$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof.

In a second embodiment of the sixth aspect of the present invention there is provided a skin whitening and skin protection against UV exposure, skin damage and aging compound of formula (5) with a formula of:

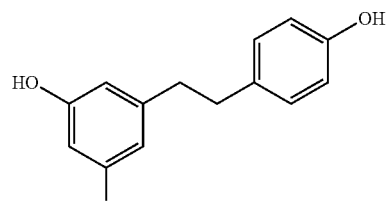
Dihydro-resveratrol

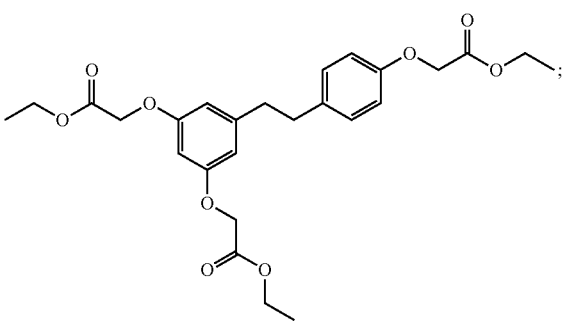
DR1

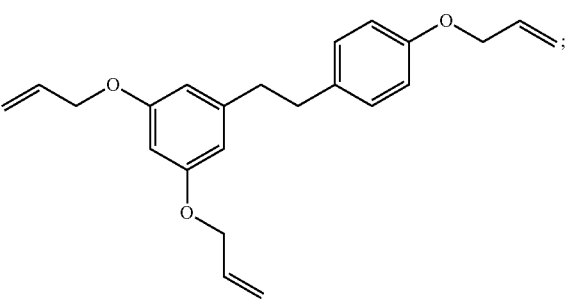
DR2

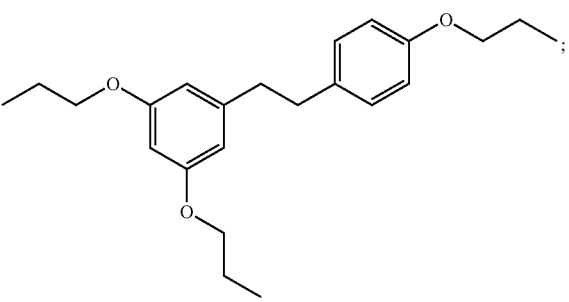
DR3

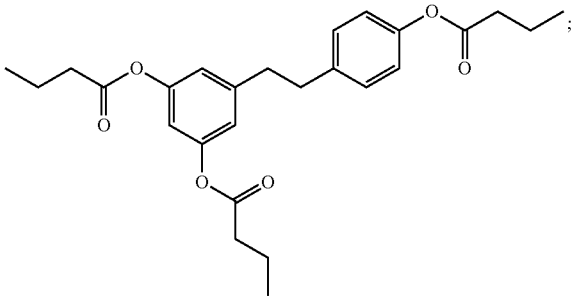
DR4

DR5
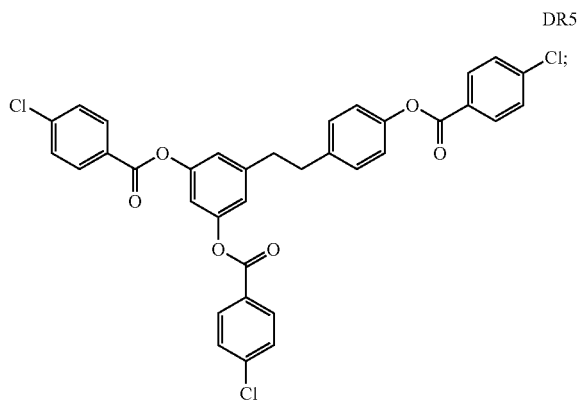

DR6
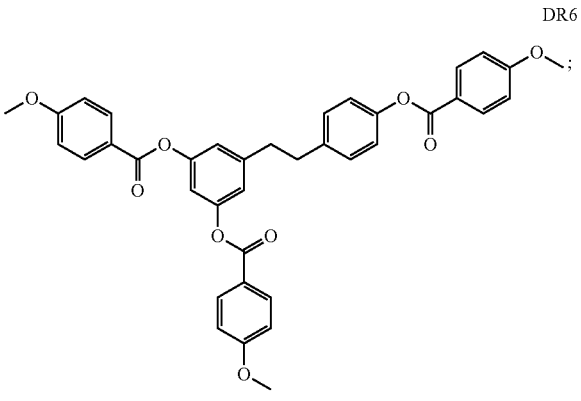

DR7
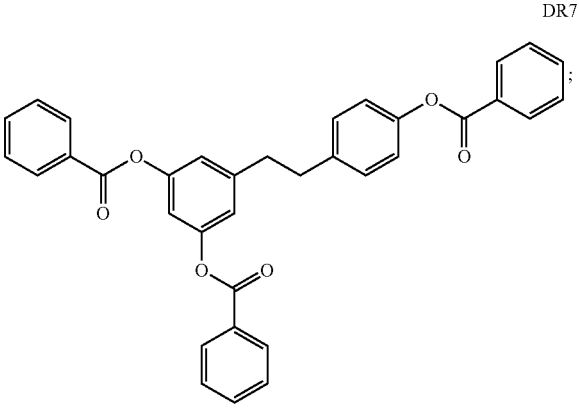

DR8
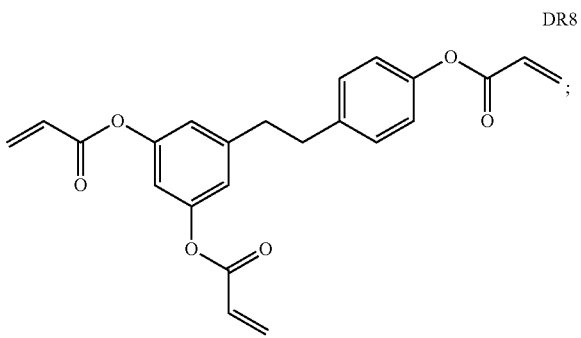

DR9
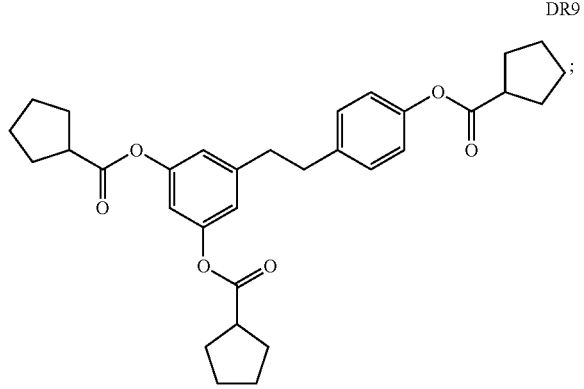

DR10
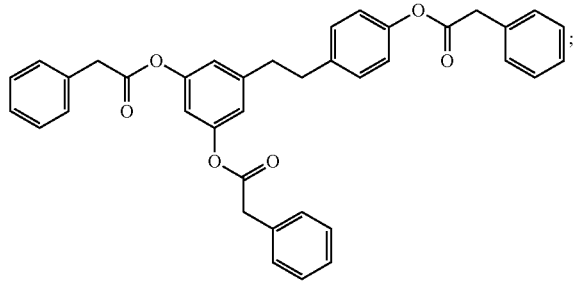

DR11
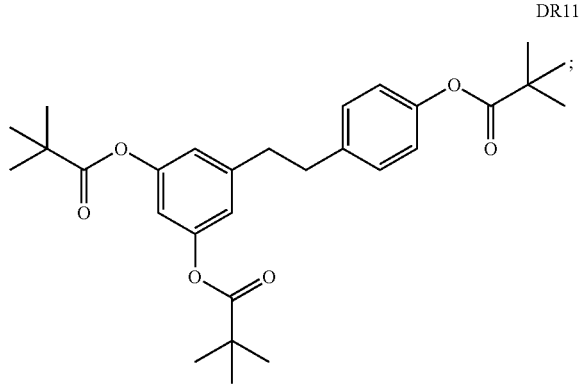

or an enantiomer thereof;

or a pharmaceutically acceptable salt or prodrug thereof.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially" of and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

DETAILED DESCRIPTION OF DRAWINGS

The above and other objects and features of the present invention will become apparent from the following description of the present invention, when taken in conjunction with the accompanying drawings, in which:

FIG. 1 shows the gain of water content in rats due to effect of pancreatic edema as a result of cerulein-induced acute pancreatitis. The obtained weights are expressed as a ratio percentage of pancreatic weight to body mass. A p-value of less than 0.05 is considered as statistically significant. *p<0.05 when comparing with control group whereas #p<0.05 comparing with cerulein group.

FIGS. 3A to 3E show the architecture and morphological alteration in pulmonary tissues of control group (FIG. 3A), cerulein group (FIG. 3B) and dihydro-resveratrol treatment groups (D-Res) (FIGS. 3C to 3E) by means of H&E staining. Images are shown with a magnification of 200×.

Figure 6A:
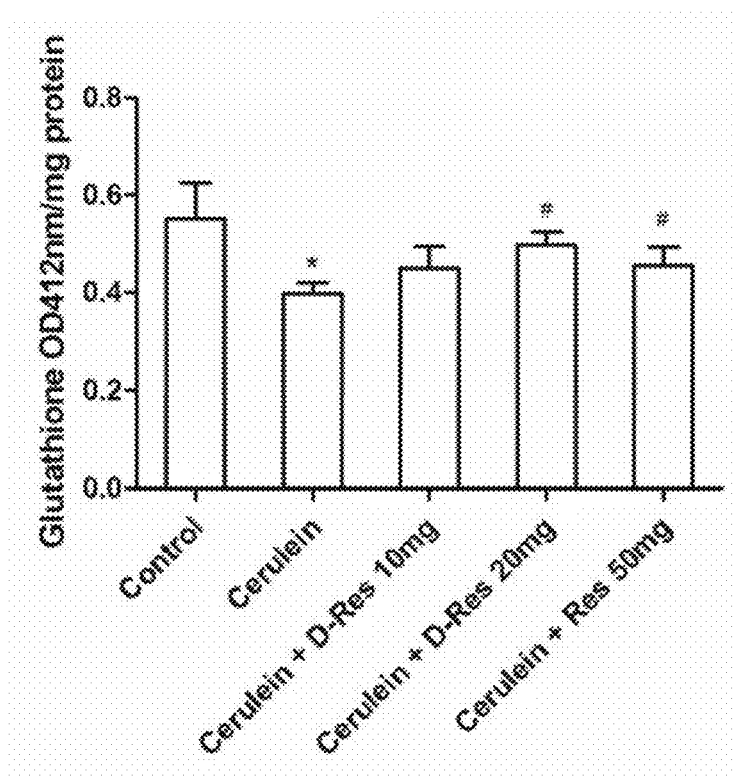
FIG. 6A shows the measurement of glutathione levels in pancreatic tissues of control group, cerulein group and dihydro-resveratrol treatment groups (D-Res) by means of colorimetric spectrophotometry. A p-value of less than 0.05 is considered as statistically significant. *p<0.05 when comparing with control group whereas #p<0.05 comparing with cerulein group.
Figure 6B:
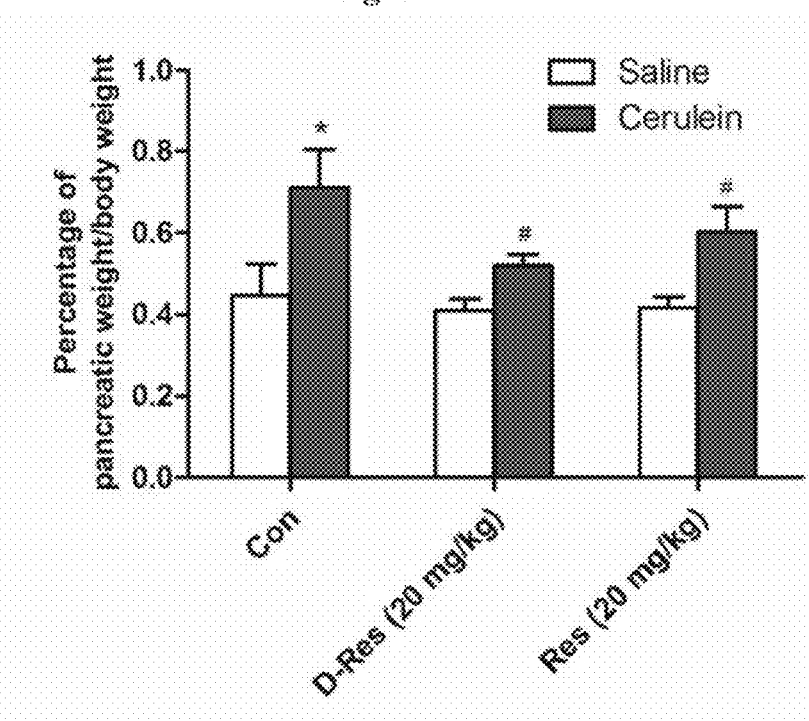

FIG. 6B shows the ameliorative effect of dihydro-resveratrol (D-res) and trans-resveratrol (Res) on reducing water content as a result of pancreatic edema in rats with cerulein-induced acute pancreatitis. The obtained weights are expressed as a ratio percentage of pancreatic weight to body mass. A p-value of less than 0.05 is considered as statistically significant. *p<0.05 when comparing with saline-treated control group (Con) whereas #p<0.05 comparing with cerulein-treated control group.

Figure 7:
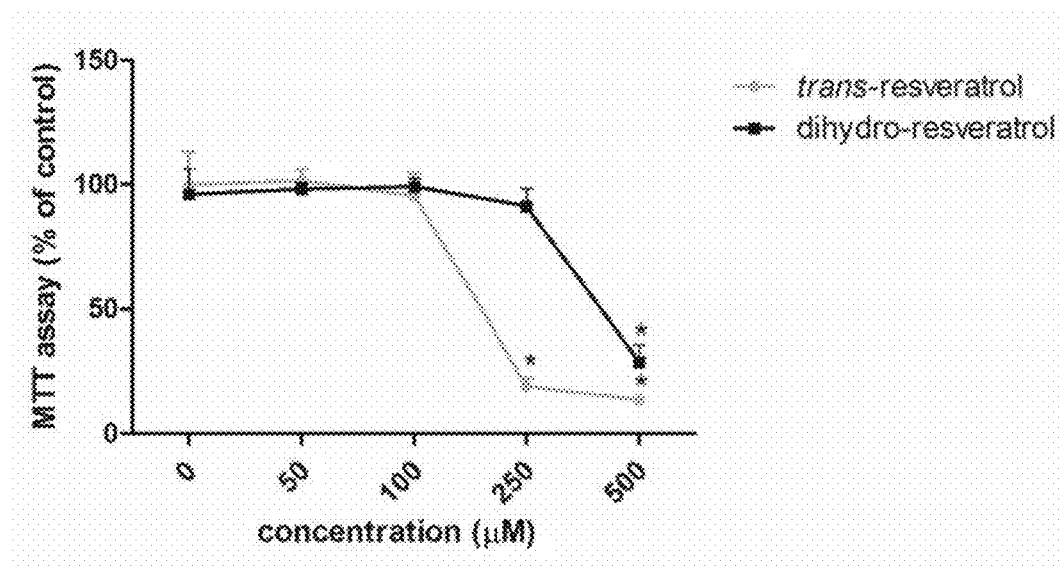

FIG. 7 shows the measurement of metabolic rates by means of MTT cell proliferation in pancreatic acinar cells treated with dihydro-resveratrol and trans-resveratrol. *p<0.05 when comparing with cells treated without dihydro-resveratrol or trans-resveratrol.

FIG. 8A to 8H shows eight derivatives (i.e. Compound i to Compound viii) from dihydro-resveratrol (i.e. Compound 2).

Figure 8A:
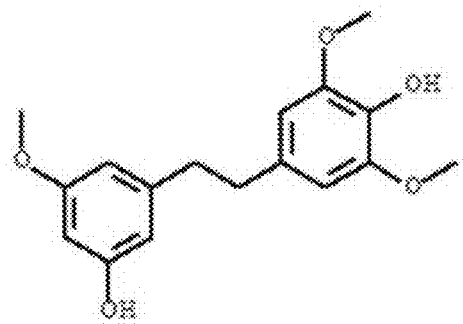
Figure 8B:
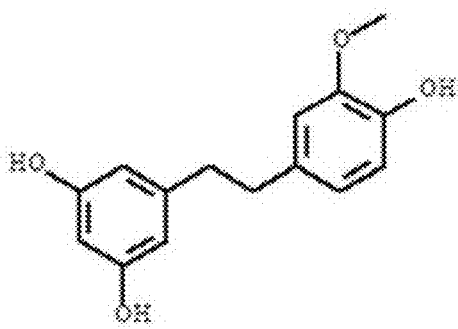
Figure 8C:
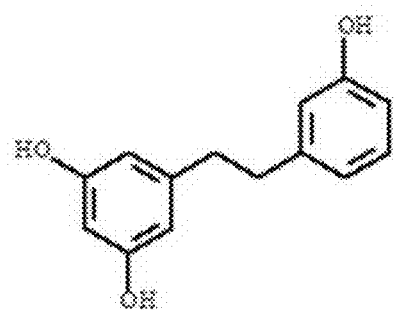
Figure 8D:
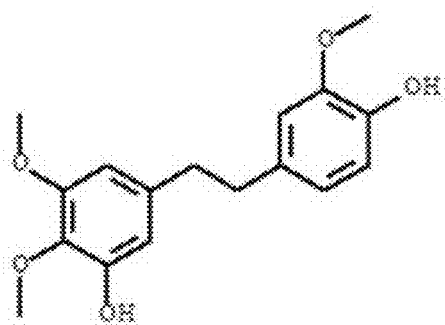
Figure 8E:
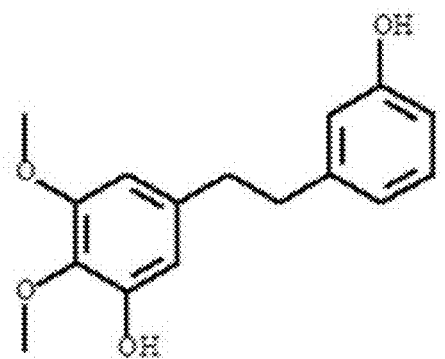
Figure 8F:
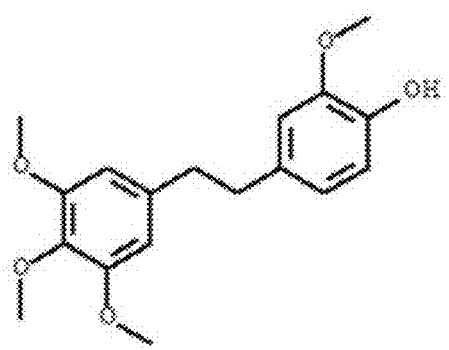
Figure 8G:
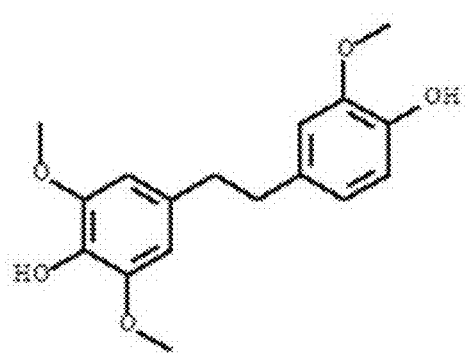
Figure 8H:
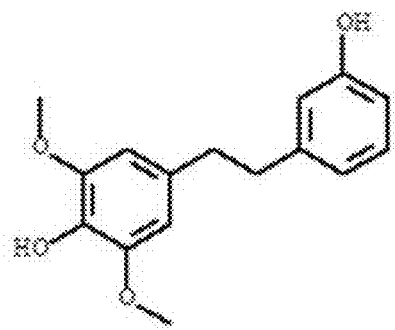
Figure 8I:
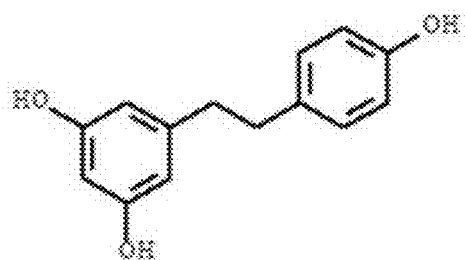

FIG. 8I shows the chemical structure of dihydro-resveratrol (i.e. Compound 2).

Figure 9:
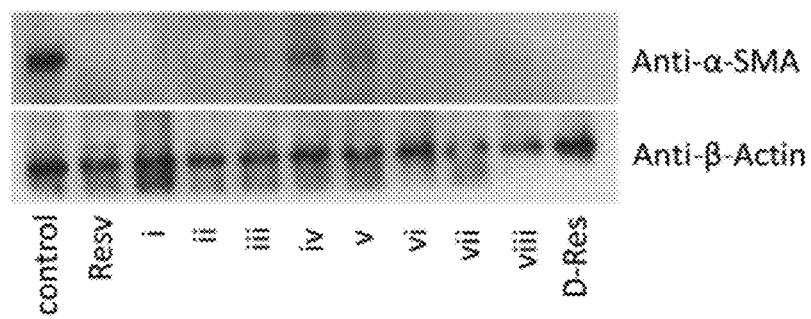

FIG. 9 shows Western blotting of LTC-14 PSCs pre-incubated with TGF-□ □ (5 ng/mL), and treated with trans-resveratrol (Resv) or dihydro-resveratrol or stilbene compounds i to viii at 20 μg/mL for 24 hours. Control was not treated with Resv or any stilbenoids.

Figure 10:
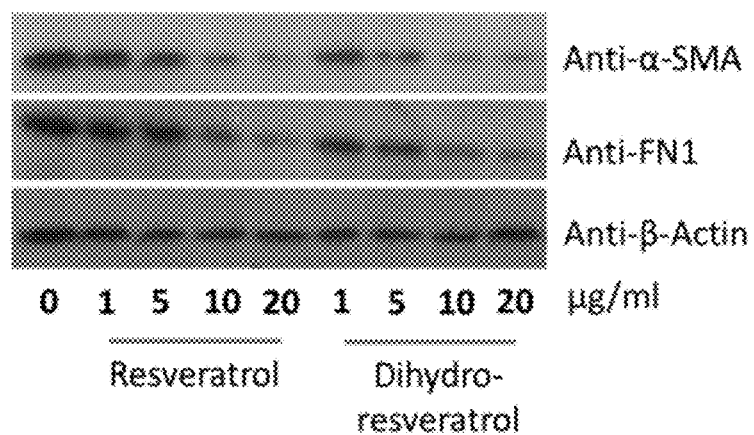

FIG. 10 shows the probing of α-SMA and FN1 in Western blotting of LTC-14 cells pre-incubated with TGF-□ (5 ng/mL), and treated with trans-resveratrol or dihydro-resveratrol at the indicated concentrations.

Figure 11:
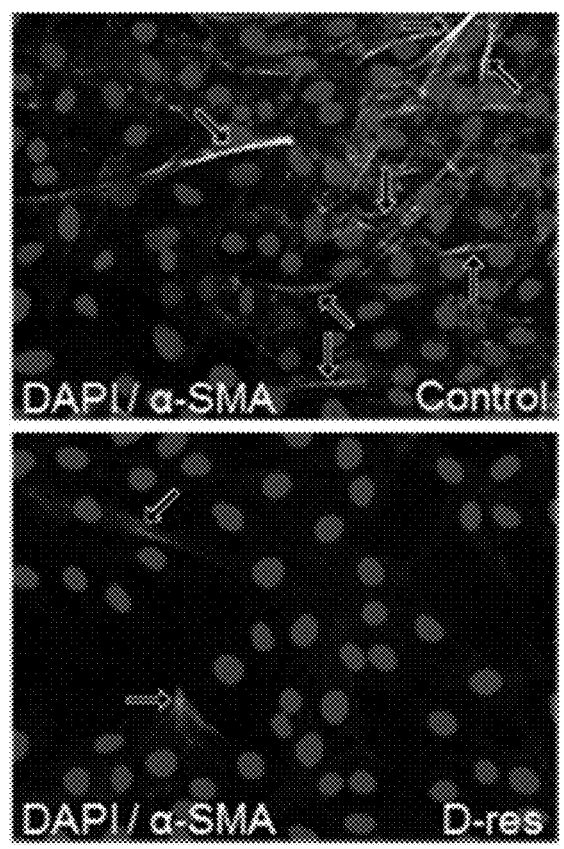

FIG. 11 shows the green fluorescent signal (identified by arrow marks) of fibrotic filaments α-SMA in LTC-14 cells implying the degree of PSC activation.

Figure 12:
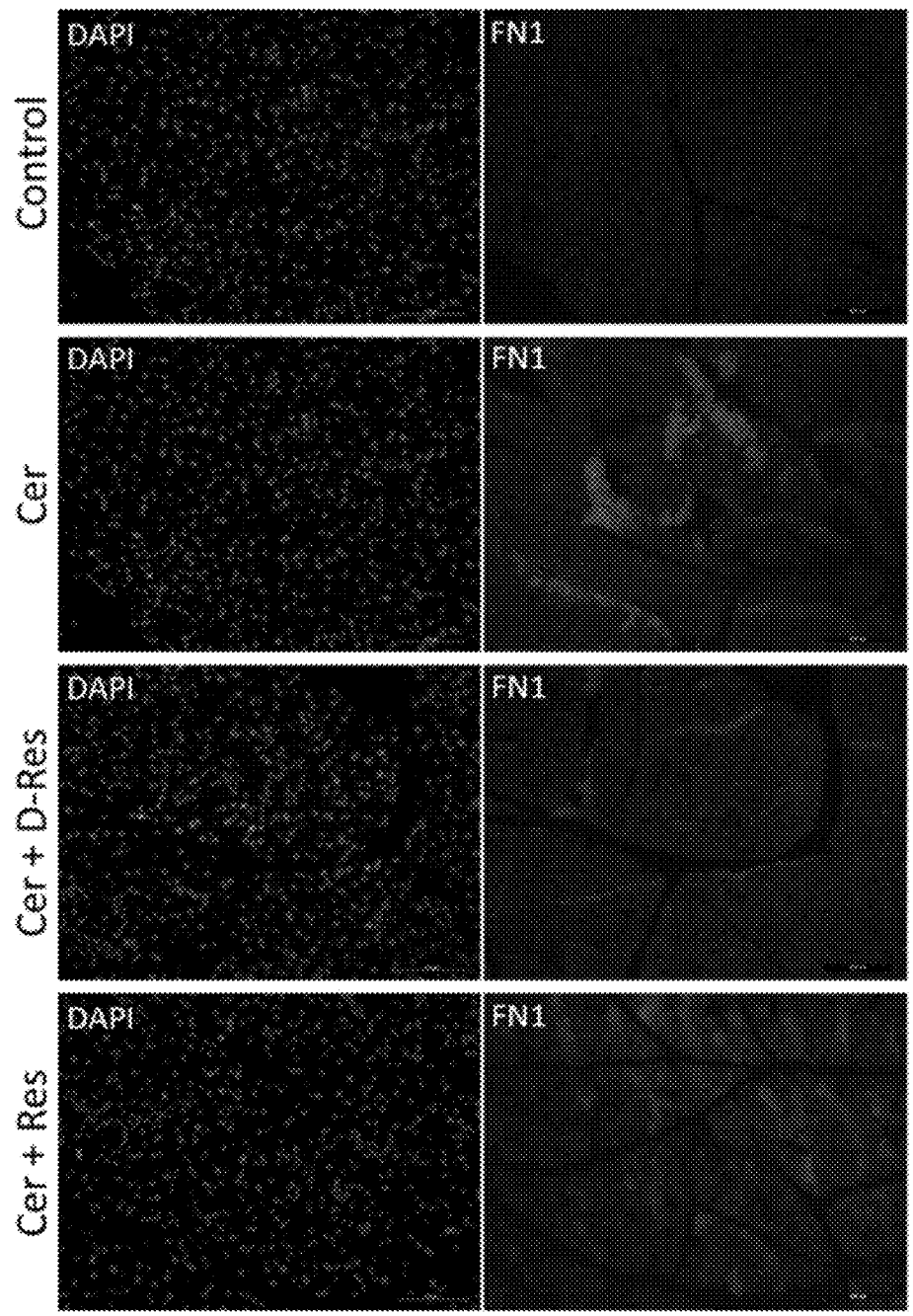

FIG. 12 shows the fluorescent signal of fibronectin (FN1) deposition in pancreatic tissue sections for an estimation of the degree of fibrosis with and without treatment of dihydro-resveratrol (D-Res, 20 mg/kg/day) or trans-resveratrol (Res, 20 mg/kg/day) in cerulein (Cer)-induced chronic pancreatitis mice.

Figure 13:
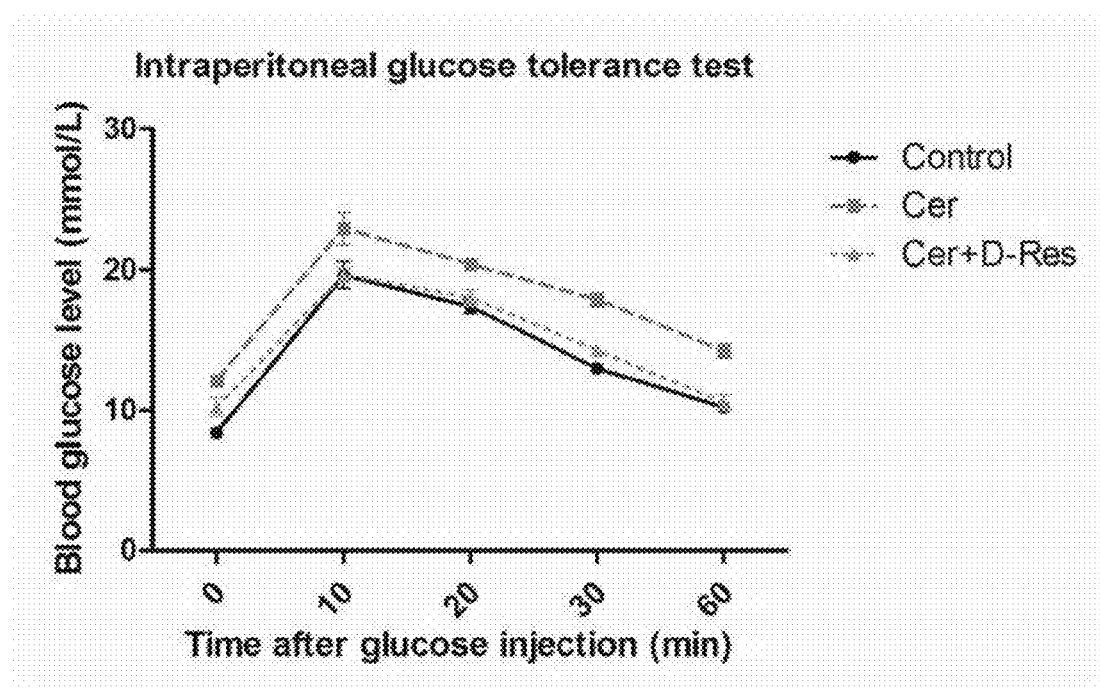

FIG. 13 shows the glucose response of the normal mice (Control) and chronic pancreatitis mice (Cer) with or without treatment of dihydro-resveratrol (D-Res, 20 mg/kg/day) in the intraperitoneal glucose tolerance test. At all time-points, a significant difference (p<0.05) is achieved between the Cer group and the Cer+D-Res group.

Figure 14:
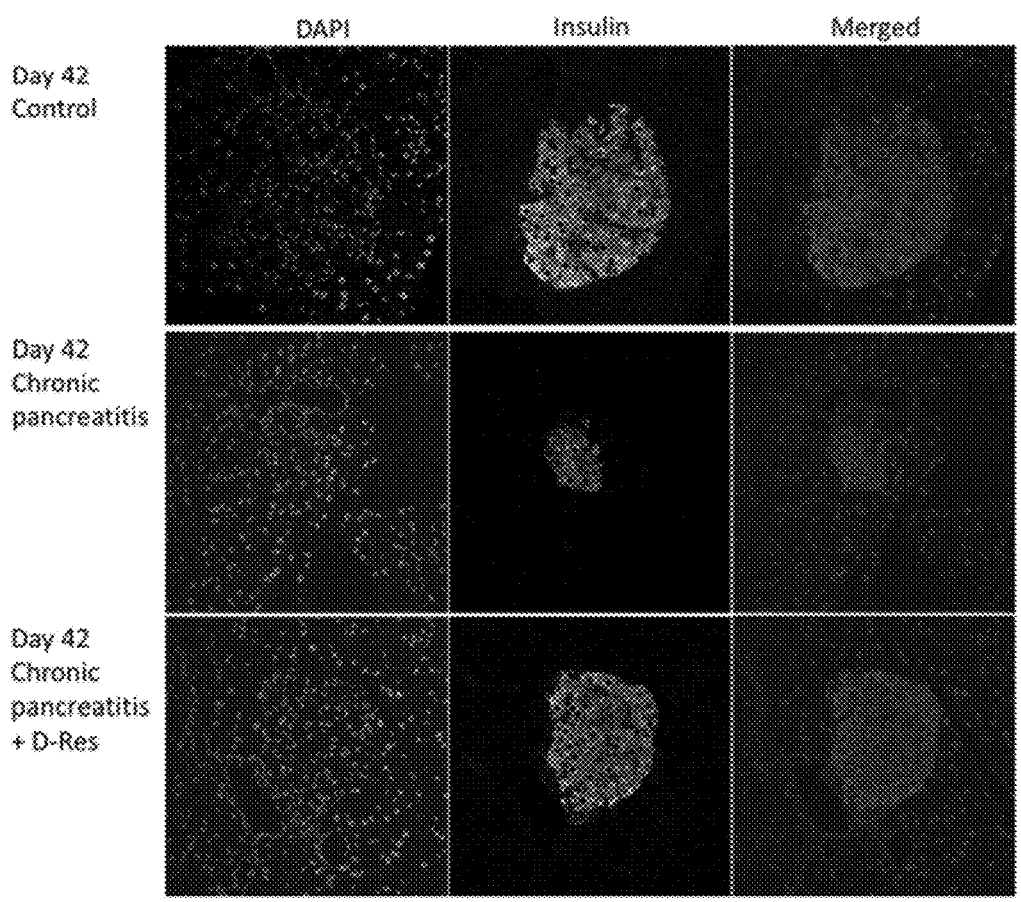

FIG. 14 shows the fluorescent signal of insulin in pancreatic tissue sections for an evaluation of pancreatic insulin-secreting cell (i.e. beta-cell) area. The comparison is made among the control mice, chronic pancreatitis mice and the chronic pancreatitis mice with treatment of dihydro-resveratrol (D-Res) at 20 mg/kg/day.

Figure 15:
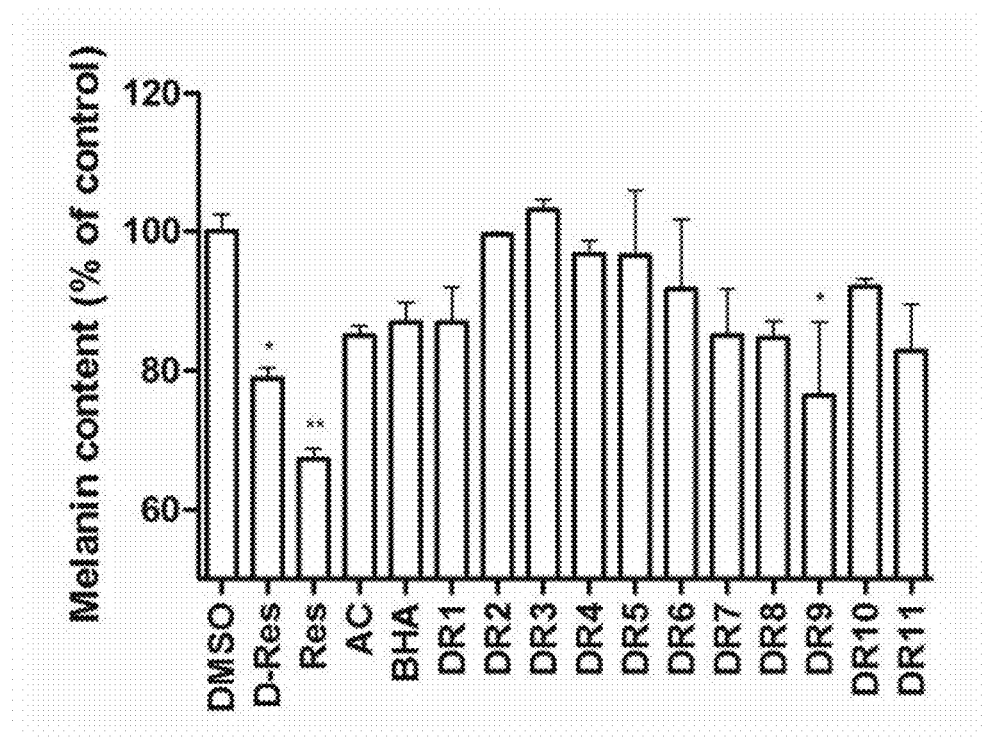

FIG. 15 shows the suppressive effect of the *Dendrobium* stilbenoids (25 μM), which are dihydro-resveratrol (D-Res), trans-resveratrol (Res) and compounds DR1 to DR11, on cellular melanin content in B16 melanocytes. Ascorbic acid (AC) and BHA are served as positive controls. Data are expressed as mean±SEM (n=3). *p<0.05 and **p<0.01 vs DMSO-treated cells.

Figure 16:
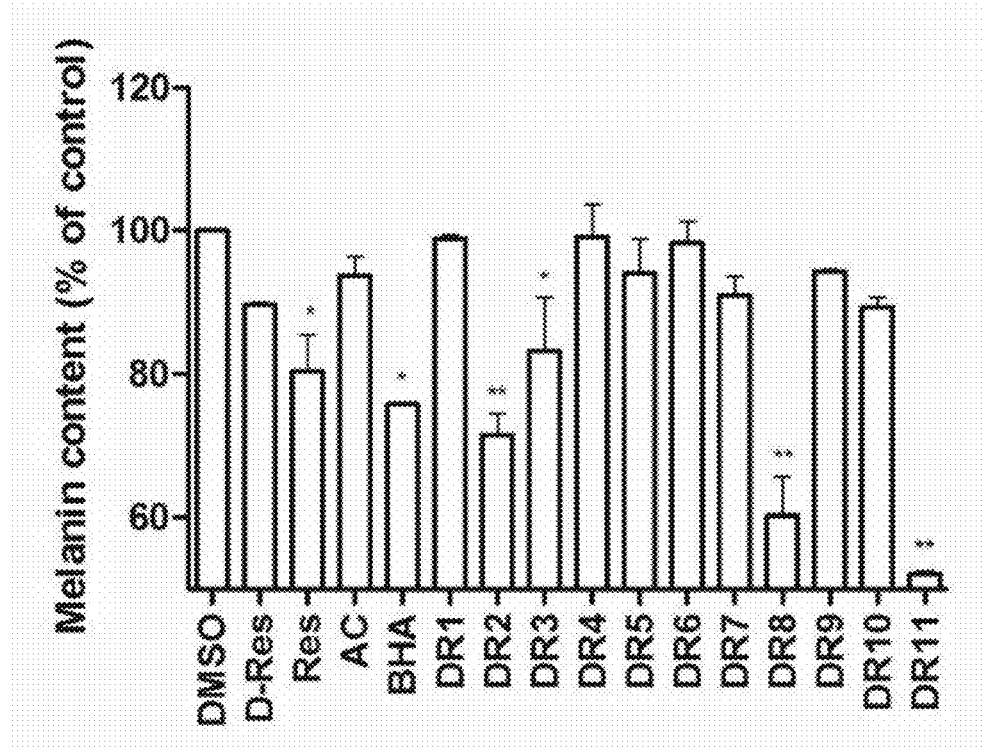

FIG. 16 shows the suppressive effect of the *Dendrobium* stilbenoids (25 μM), which are dihydro-resveratrol (D-Res), trans-resveratrol (Res) and compounds DR1 to DR11, on cellular melanin content in A375 melanocytes. Ascorbic acid (AC) and BHA are served as positive controls. Data are expressed as mean±SEM (n=3). *p<0.05 and **p<0.01 vs DMSO-treated cells.

Figure 17:
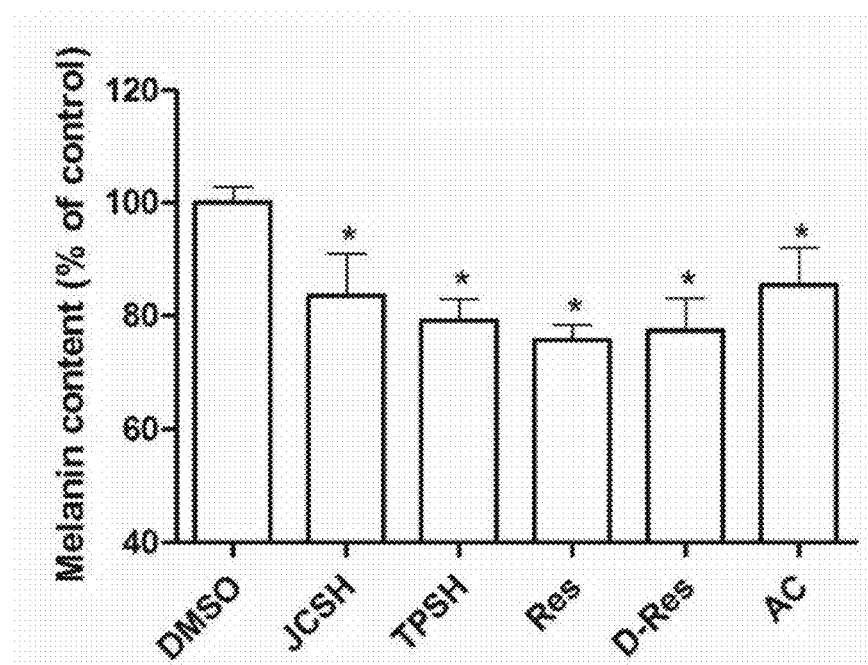

FIG. 17 shows the suppressive effect of *D. nobile* extract (JCSH, 50 µg/mL), *D. officinale* extract (TPSH, 50 µg/mL), trans-resveratrol (Res, 25 µM) and dihydro-resveratrol (D-Res, 25 µM) on cellular melanin content in B16 melanocytes. Ascorbic acid (AC) is served as a positive control. Data are expressed as mean±SEM (n=3). *p<0.05 vs DMSO-treated cells.

Figure 18:
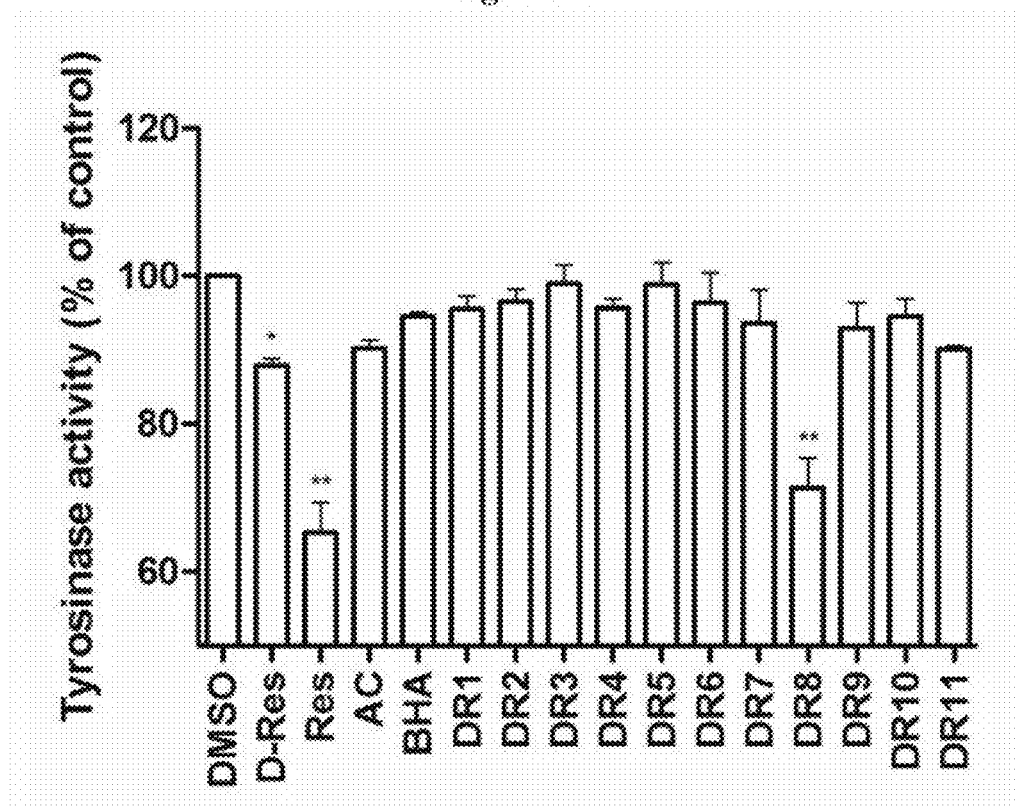

FIG. 18 shows the inhibitory effect of the *Dendrobium* stilbenoids (25 µM), which are dihydro-resveratrol (D-Res), trans-resveratrol (Res) and compounds DR1 to DR11, on cellular tyrosinase activity in B16 melanocytes. Ascorbic acid (AC) and BHA are served as positive controls. Data are expressed as mean±SEM (n=3). *p<0.05 and **p<0.01 vs DMSO-treated cells.

Figure 19:
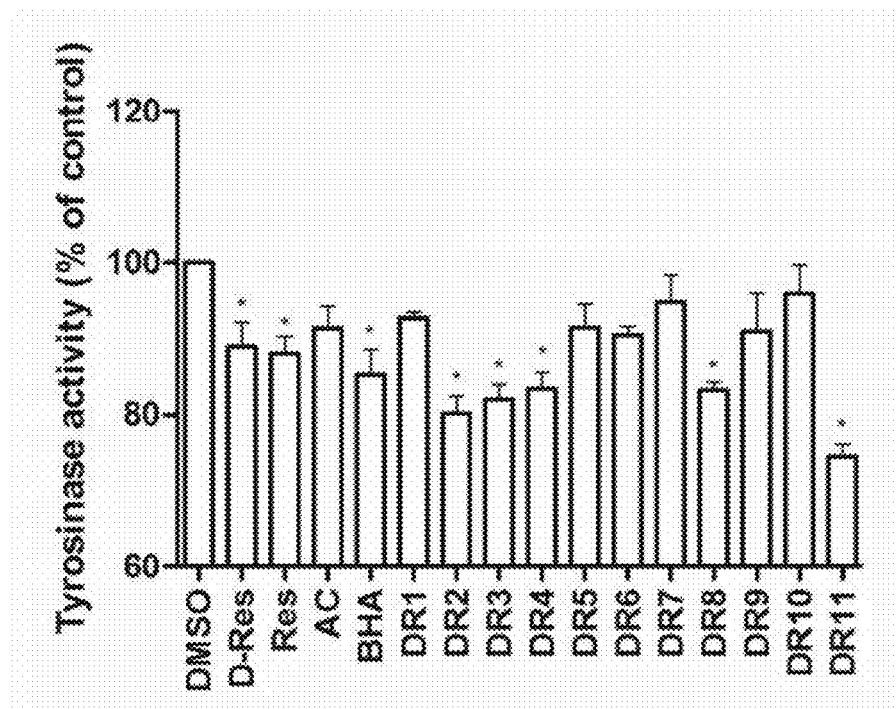

FIG. 19 shows the inhibitory effect of the *Dendrobium* stilbenoids (25 µM), which are dihydro-resveratrol (D-Res), trans-resveratrol (Res) and compounds DR1 to DR11, on cellular tyrosinase activity in A375 melanocytes. Ascorbic acid (AC) and BHA are served as positive controls. Data are expressed as mean±SEM (n=3). *p<0.05 vs DMSO-treated cells.

Figure 20:
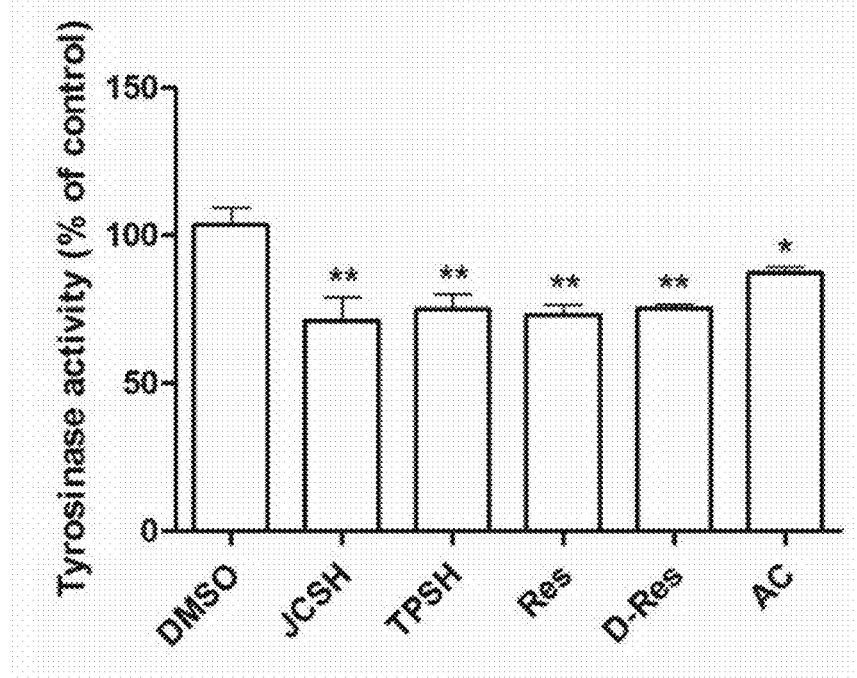

FIG. 20 shows the inhibitory effect of *D. nobile* extract (JCSH, 50 µg/mL), *D. officinale* extract (TPSH, 50 µg/mL), trans-resveratrol (Res, 25 µM) and dihydro-resveratrol (D-Res, 25 µM) on cellular tyrosinase activity in B16 melanocytes. Ascorbic acid (AC) is served as a positive control. Data are expressed as mean±SEM (n=3). *p<0.05 and **p<0.01 vs DMSO-treated cells.

Figure 21:
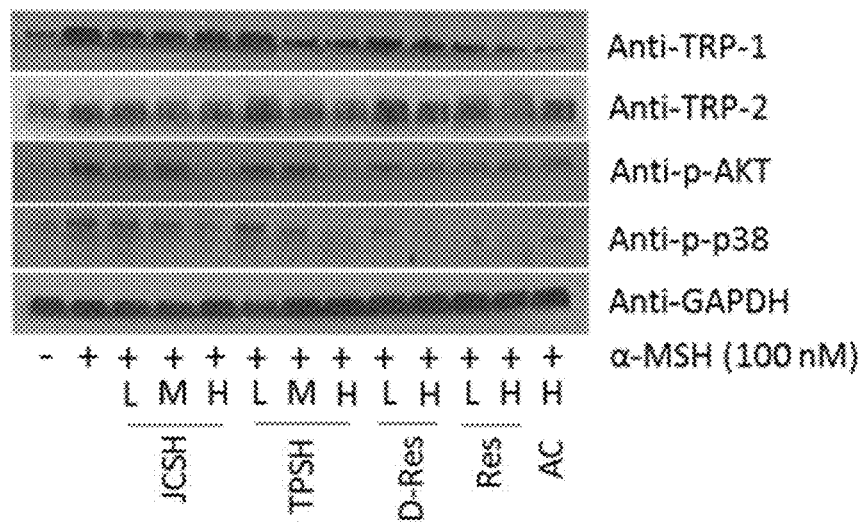

FIG. 21 shows suppressive effect of *D. nobile* extract (JCSH, L:10; M:25; H:50 µg/mL) and *D. officinale* extract (TPSH, L:10; M:25; H:50 µg/mL), dihydro-resveratrol (D-Res, L:25; H:50 µM), trans-resveratrol (Res, L:25; H:50 µM) and ascorbic acid (AC, H:50 µg/mL) on protein levels of TRP-1, TRP-2, phospho-AKT and phospho-p38 in B16 melanocytes. GAPDH is served as a loading reference.

Figure 22:
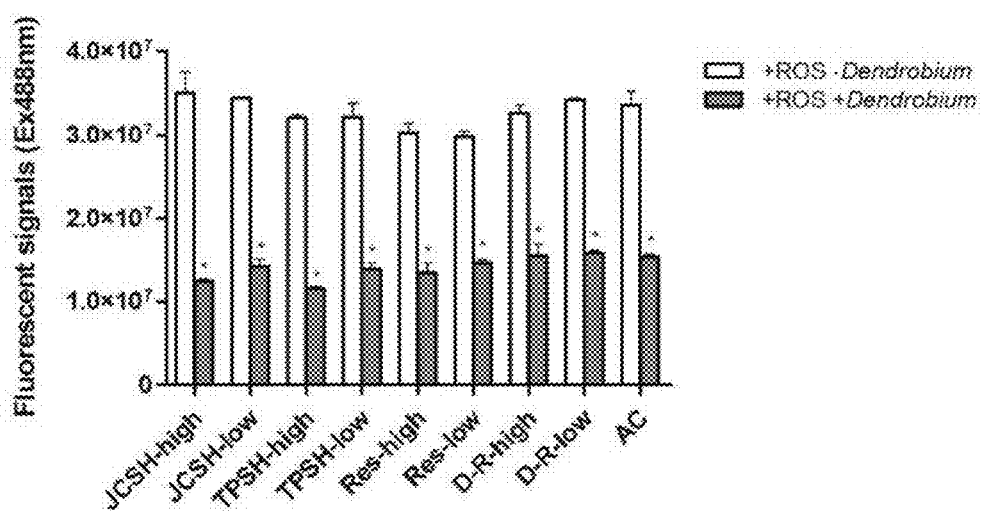

FIG. 22 shows suppressive effect of *D. nobile* extract (JCSH, high: 50 µg/mL; low: 25 µg/mL), *D. officinale* extract (TPSH, high: 50 µg/mL; low: 25 µg/mL), trans-resveratrol (Res, high: 50 µM; low: 25 µM), dihydro-resveratrol (D-R, high: 50 µM; low: 25 µM) and ascorbic acid (AC, 50 µM) on ROS generation in B16 melanocytes. Fluorescent signals are measured at Ex 488 nm. Data are expressed as mean±SEM (n=3). *p<0.05 vs the sole TBHP treatment (i.e. no *Dendrobium* extract or compound).

Figure 23:
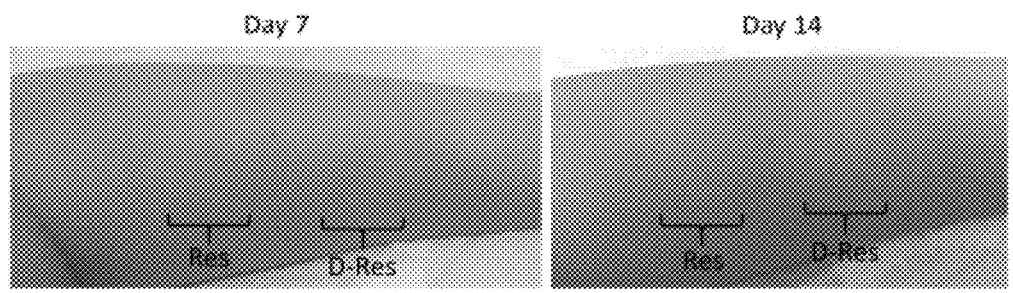

FIG. 23 shows the whitening effect of stilbenoid solution containing 2% trans-resveratrol (Res) or 2% dihydro-resveratrol (D-Res) on the arm of an individual human subject on day 7 and day 14.

DETAILED DESCRIPTION OF INVENTION

The present invention is not to be limited in scope by any of the specific embodiments described herein. The following embodiments are presented for exemplification only.

Definitions

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The term "alkyl" as used herein includes reference to a straight or branched chain alkyl moiety having 1, 2, 3, 4, 5, 6, 7, 8, 9, 10, 11, 12, 13, 14, 15, 16, 17, 18, 19 or 20 carbon atoms. Examples of alkyl groups include "$C_{1-6}$ alkyl" and "$C_{2-10}$ alkyl". The term "$C_{1-6}$ alkyl" as used herein include reference to a straight or branched chain alkyl moiety having 1, 2, 3, 4, 5 or 6 carbon atoms. The term "$C_{2-10}$ alkyl" as used herein include reference to a straight or branched chain alkyl moiety having 1, 2, 3, 4, 5, 6, 7, 8, 9 or 10 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3, 4, 5 or 6 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbomyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1, 2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

Among the several established animal models, repetitive intraperitoneal (i.p.) injection of cholecystokinin secretagogue, cerulein, is the most widely used and a highly reproducible method for the production of an experimental acute pancreatitis. Followed by a single shot of lipopolysaccharide (LPS), pulmonary injury characterized by neutrophil sequestration in the lung tissues and increased permeability of the alveolar membrane barrier is often observed as an acute pancreatitis associated complication. For the diagnosis of the onset of acute pancreatitis, bulky leakage of digestive enzymes, namely α-amylase, into the bloodstream is regarded as the principal pathological parameter. For evaluating the severity of acute pancreatitis and the associated pulmonary injury, morphological alterations of organ architecture including interstitial edema, cellular damage, leukocyte infiltration and hemorrhage are characterized as the histological and/or pathological parameters. Besides histological examination, aberrant MPO activity is often measured for assessing the severity of neutrophil-mediated inflammatory condition. Both the local and systemic inflammatory responses can be further confirmed by the high levels of pro-inflammatory cytokines present in the homogenates of affected tissues. Moreover, glutathione depletion, a defense mechanism, is one of the most common parameters for assessing the severity of tissue injury.

The subject to be treated by the method of this invention may be a human or an animal. The present invention is applicable to various forms of acute pancreatitis, and particularly to the acute pancreatitis associated systemic complications including pulmonary injury.

Dihydro-resveratrol, also known as trans-3,5,4'-trihydroxybibenzyl, is a derivative of polyphenol belonging to the family of stilbenoids, which are often obtained from plant extracts. In fact, dihydro-resveratrol is a phytoalexin produced by various plant species including Orchidaceae and *Cannabis sativa* L. against abiotic and biotic challenges, particularly in the case of fungal infection as reported in Fritzemeier, K. H., Kindl, H. 1983. 9,10-dihydrophenanthrenes as phytoalexins of Orchidaceae. Biosynthetic studies in vitro and in vivo proving the route from L-phenylalanine to dihydro-m-coumaric acid, dihydrostilbene and dihydrophenanthrenes. Eur J Biochem 133, 545-550.

The present invention relates to the usage of a polyphenol derivative of the stilbenoid family with formula 1:

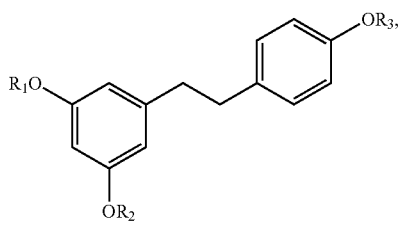

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, to ameliorate tissue injury of the pancreas and lungs.

The present invention further relates to the usage of a stilbene compound containing trans-3,5,4'-trihydroxybibenzyl, also known as dihydro-resveratrol, see Compound 2:

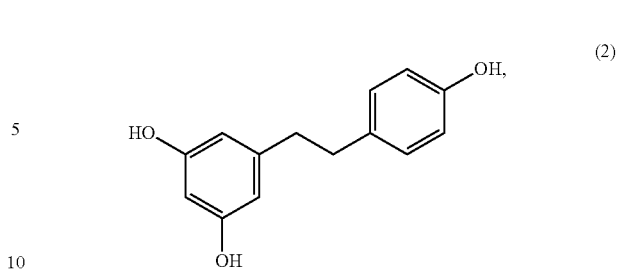

to ameliorate tissue injury of the pancreas and lungs. In the present invention, this particular stilbenoid derivative was obtained as white powders through dehydrogenation of trans-resveratrol.

Further, the invention is concerned with a process for the manufacture of the above compound, pharmaceutical preparations which contain such compound, and the use of this compound for the production of pharmaceutical preparations.

Figure 1:
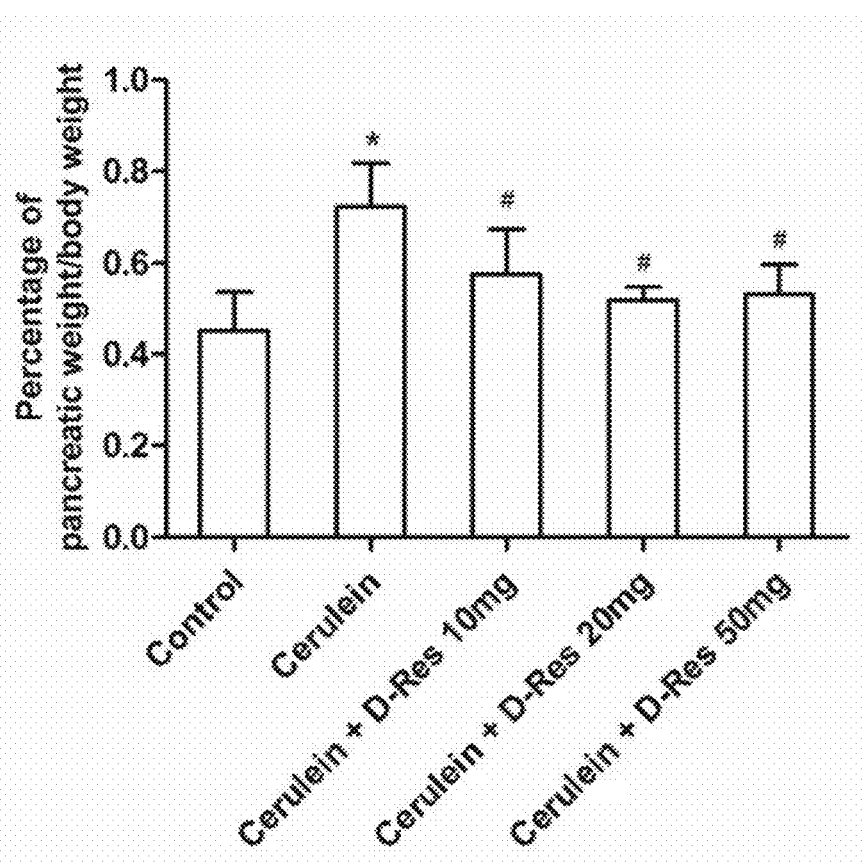
Figures 2A, 2B:
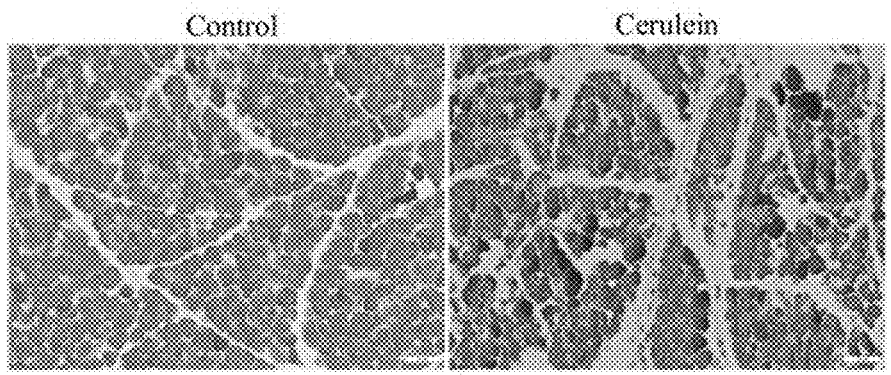
FIGS. 2A to 2F show the architecture and morphological alteration in pancreatic tissues of control group (FIG. 2A), cerulein group (FIG. 2B) and dihydro-resveratrol treatment groups (D-Res) (FIGS. 2C to 2F) by means of hematoxylin and eosin (H&E) staining. Images are shown with a scale bar of 50 μm.
Figures 2C, 2D:
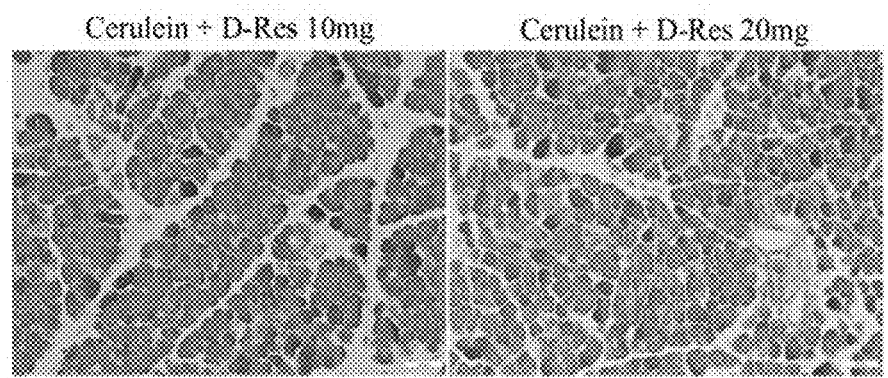
Figures 2E, 2F:
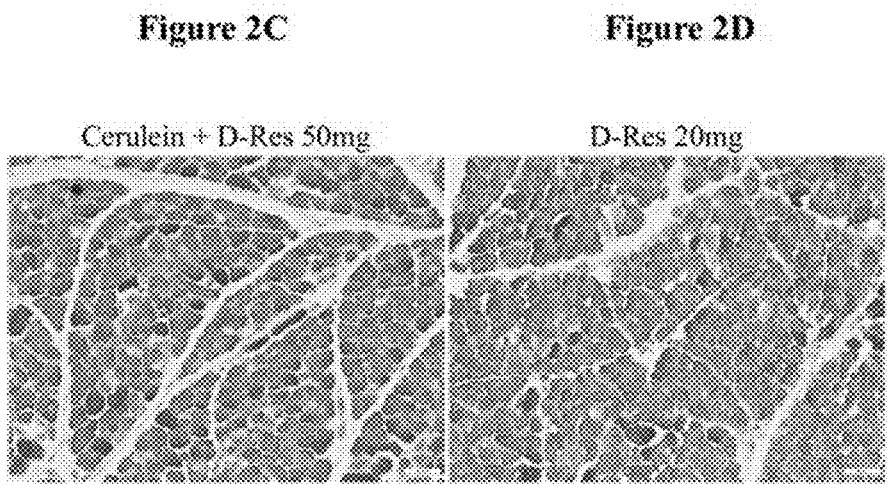

The oral administration of dihydro-resveratrol at an adequate dosage of not less than 20 mg/kg is shown to significantly ameliorate the severity of acute pancreatitis and associated pulmonary injury in cerulein-treated rats. In terms of pathological parameters, rats with acute pancreatitis are shown to have lessened pancreatic water content due to an attenuation of pancreatic edema (FIG. 1), lowered plasma level of α-amylase (Table 1), more intact acinar morphology (FIGS. 2C to 2F) and reduced thickening of alveolar wall and hemorrhage (FIGS. 3C to 3E).

TABLE 1

Plasma α-amylase activities are expressed as U/µl/minute. A p-value of less than 0.05 is considered as statistically significant and S.D. stands for standard derivation.

|  | Control | Cerulein | Cerulein + D-Res 10 mg | Cerulein + D-Res 20 mg | Cerulein + D-Res 50 mg |
| --- | --- | --- | --- | --- | --- |
| mean | 0.1294 | 0.4846 * | 0.2891 | 0.2498 # | 0.2431 # |
| S.D. | 0.03909 | 0.1457 | 0.05248 | 0.05593 | 0.06025 |

* $p < 0.05$ when comparing with control group whereas
$p < 0.05$ comparing with cerulein group.

Figure 4A:
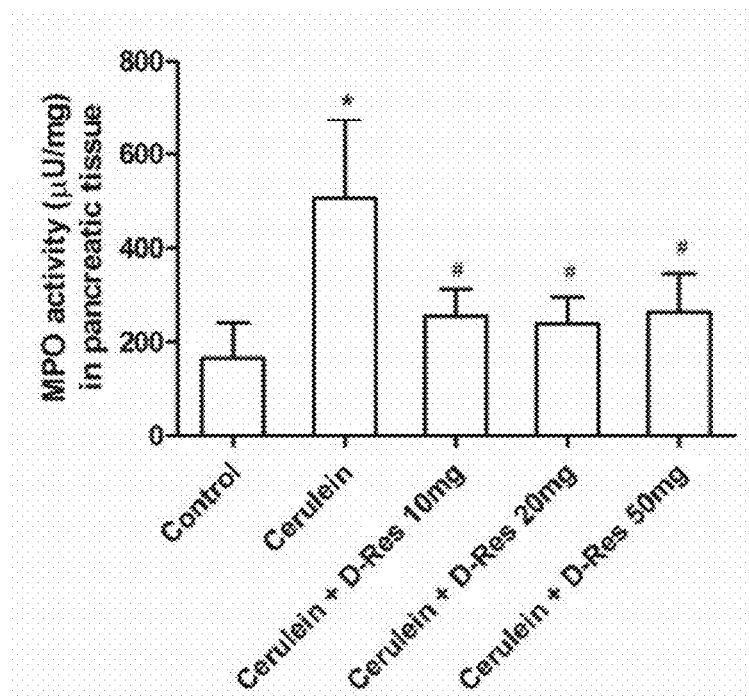
FIG. 4A shows the measurement of MPO activity which represents neutrophil sequestration in pancreatic tissues of control group, cerulein group and dihydro-resveratrol treatment groups (D-Res) by means of colorimetric spectrophotometry. A p-value of less than 0.05 is considered as statistically significant. *p<0.05 when comparing with control group whereas #p<0.05 comparing with cerulein group.
Figure 4B:
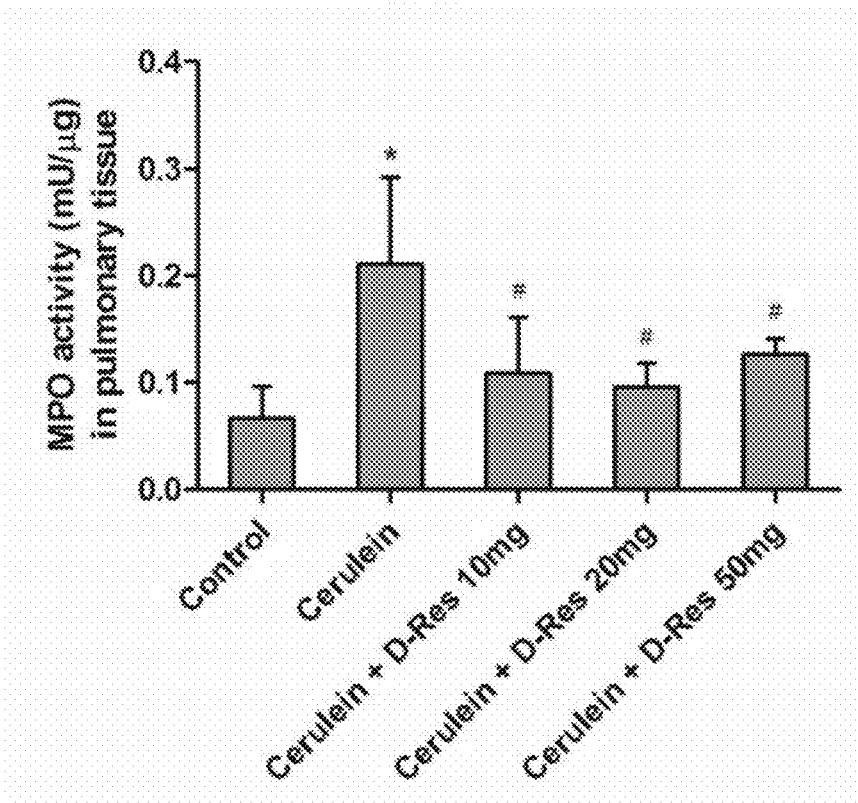
FIG. 4B shows the measurement of MPO activity which represents neutrophil sequestration in pulmonary tissues of control group, cerulein group and dihydro-resveratrol treatment groups (D-Res) by means of colorimetric spectrophotometry. A p-value of less than 0.05 is considered as statistically significant. *p<0.05 when comparing with control group whereas #p<0.05 comparing with cerulein group.
Figure 5A:
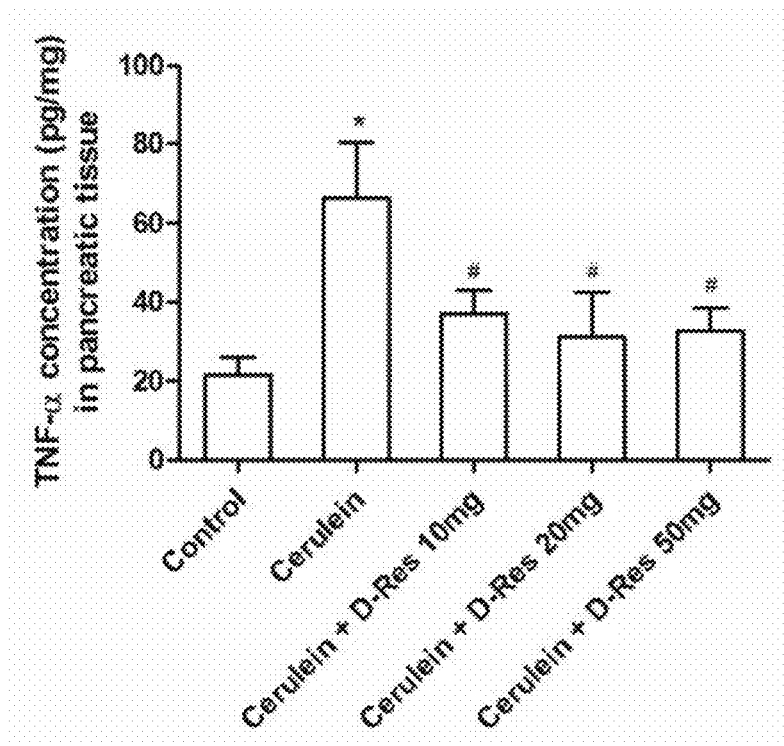
FIG. 5A shows the measurement of TNF-α level in pancreatic tissues of control group, cerulein group and dihydro-resveratrol treatment groups (D-Res) by means of enzyme-linked immunosorbent assay (ELISA). A p-value of less than 0.05 is considered as statistically significant. *p<0.05 when comparing with control group whereas #p<0.05 comparing with cerulein group.
Figure 5B:
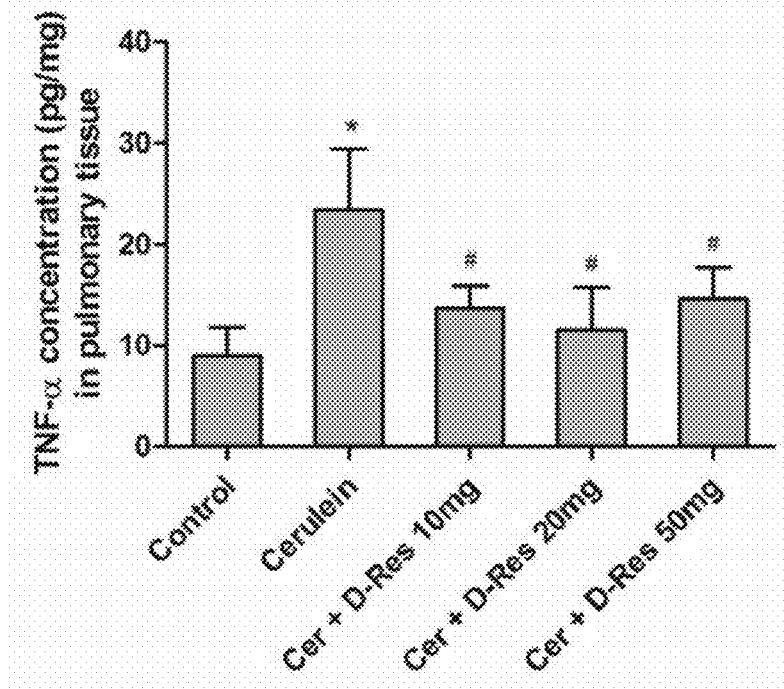
FIG. 5B shows the measurement of TNF-α level in pulmonary tissues of control group, cerulein group and dihydro-resveratrol treatment groups (D-Res) by means of ELISA. A p-value of less than 0.05 is considered as statistically significant. *p<0.05 when comparing with control group whereas #p<0.05 comparing with cerulein group.

Cerulein-induced elevated levels of neutrophil sequestration, which is quantified as the activity of MPO, are significantly suppressed in pancreatic and pulmonary tissues by the administration of dihydro-resveratrol (FIGS. 4A and 4B). Cerulein-induced elevated levels of TNF-α in the pancreas and lungs are significantly suppressed by the administration of dihydro-resveratrol (FIGS. 5A and 5B).

Glutathione depletion is a distinctive sign of tissue injury. The cerulein-induced declined levels of glutathione in the pancreas are significantly restored by the administration of dihydro-resveratrol (FIG. 6A).

In the present invention, dihydro-resveratrol completely and easily dissolves in 0.5% (weight/volume, w/v) methanol whereas trans-resveratrol, with vigorous shaking, dissolves in 2.5% (w/v) methanol (Table 2). Thus, the solubility of dihydro-resveratrol is at least 5 times higher than that of trans-resveratrol. The ameliorative effect of dihydro-resveratrol was more promising than that of trans-resveratrol on reducing water content as a result of pancreatic edema in rats with cerulein-induced acute pancreatitis (FIG. 6B).

TABLE 2

Solubility of Dihydro-resveratrol and Trans-resveratrol in methanol.

|  | Trans-resveratrol | Dihydro-resveratrol |
|---|---|---|
| Methanol required (w/v) | 2.5% | 0.5% |

From the evaluation of mitochondrial metabolic rates by means of MTT assay, the cytotoxicity of dihydro-resveratrol in pancreatic acinar cells is determined to be approximately 500 μM whereas that of trans-resveratrol is roughly 250 μM (FIG. 7). Thus, the cytotoxicity of dihydro-resveratrol was 50% lower than that of trans-resveratrol.

Experiments

Preparation and structural identification of dihydro-resveratrol. The molecular formula of dihydro-resveratrol was established as $C_{14}H_{14}O_3$, which was obtained as white powders through hydrogenation of trans-resveratrol. A solution of trans-resveratrol (10 g, 43.8 mmol) in anhydrous EtOH (150 ml) was stirred at room temperature under 5 atm $H_2$ pressure in the presence of 10% Pd/C (0.2 g). The reaction was quenched after 8 hours (h), by filtering off the catalyst. The filtrate was evaporated in vacuum and the residue was subjected to silica gel chromatographic separation eluting with petroleum ether and ethyl acetate (1:1) to afford dihydro-resveratrol as white amorphous powder (9.6 g, 95% yield): HR-ESIMS ([M+1]+ m/z 231.1026, calcd 231.1016 for $C_{14}H_{15}O_3$); $^1$H NMR (methanol-d4, 400 MHz) δ 6.96 (2H, ABd, J=8.3 Hz), 6.67 (2H, ABd, J=8.4 Hz), 6.13 (2H, brd, J=2.2 Hz), 6.09 (1H, brt, J=2.2 Hz), 2.74 (2H, brdd, J=8.5, 5.6), 2.67 (2H, brdd, J=8.3, 5.2); $^{13}$C NMR (methanol-d4, 100 MHz) δ 159.2 (2C, s), 156.3 (1C, s), 145.6 (1C, s), 134.1 (1C, s), 130.3 (2C, d), 116.0 (2C, d), 108.1 (2C, d), 101.1 (1C, d), 39.6 (2C, t), 38.0 (2C, t).

Evaluation of biological activities. Sprague-Dawley rats aged 28 days weighing in the range of 70 to 90 g were randomly assigned into 6 groups of 6 to 8 individuals. The rats were housed with an ambient temperature of 23±2° C., a relative humidity of 60 to 80% and a 12-h light/dark cycle. Prior to the experiment, the rats were starved overnight but allowed with free access to water. Experimental acute pancreatitis was induced in the rats by six hourly i.p. injections of cerulein at the supramaximally stimulating dose (50 μg/kg) followed by a single dose of LPS at 7.5 mg/kg 1 h after the last cerulein injection, and this group of rats was designated as the cerulein group. The control group received injections of 0.9% saline instead of cerulein in the same volume and at same time intervals. The treatment groups given with cerulein and oral doses of dihydro-resveratrol (10, 20 or 50 mg/kg) were designated as Cerulein+D-res 10 or 20 or 50 mg/kg. The therapeutic intervention was given 30 minutes after the first cerulein injection for three consecutive hours. Upon scarification, pancreata were immediately removed, weighed, trimmed from fat and fixed in 4% paraformaldehyde-phosphate buffered saline overnight at 4° C. Samples were then processed, embedded in paraffin wax, sectioned and subjected to H&E staining. Levels of TNF-α in pancreatic and pulmonary samples were determined using commercial ELISA kits. Tissue homogenates were subjected to biochemical assays for the evaluation of MPO activity and glutathione content.

Functional intact acini were dissociated from pancreatic tissue using collagenase digestion with mild shearing forces. Acini were cultured in Dulbecco's modification of Eagle's medium (GIBCO) supplemented with 5% fetal bovine serum (GIBCO), 1% penicillin-streptomycin (GIBCO) in a 5% $CO_2$, 95% air humidified atmosphere at 37° C. LTC-14 cells were seeded at a density of $1 \times 10^4$/well in a 96-well plate, and incubated with different concentrations of dihydro-resveratrol or trans-resveratrol (dissolved in DMSO) for 24 hours. MTT reagent was added to the cells at the end of the 24-hour treatment period. After a 3-hour reaction time, MTT products were dissolved in DMSO and absorbance at 570 nm was taken.

Results

After the induction of cerulein, the weight ratio of pancreas to body in the acute pancreatitis rats was drastically increased by roughly 60% when compared with the non-cerulein induced controls due to the occurrence of pancreatic edema. The oral administration of dihydro-resveratrol at an adequate dosage of not less than 20 mg/kg notably reduced the pancreatic edema as reflected by the significant decrease in the weight ratio of pancreas to body. The ameliorative effect of dihydro-resveratrol on reducing pancreatic edema was more promising than that of trans-resveratrol, the accredited antioxidant. Regarding the human dosage, the comparable dosage is 3.24 mg/kg based on the standard dosage conversion according to Reagan-Shaw S, Nihal M, Ahmad N (2008) Dose translation from animal to human studies revisited. FASEB J 22(3): 659-661.

When oral administration of dihydro-resveratrol was given, the focal expansion of the interlobular septae, cytoplasmic shrinkage and leukocyte infiltration in pancreatitic parenchyma was remarkably reduced whereas the pulmonary wall thickening and hemorrhage in lung tissues were significantly improved in the rats with cerulein-induced acute pancreatitis.

For a relief of inflammatory conditions of the pancreas and lungs, the levels of pro-inflammatory cytokine TNF-α as well as MPO activities were significantly reduced in the pancreatic and pulmonary tissues by the oral administration of dihy dro-resveratrol.

The level of glutathione in cerulein-induced pancreatic tissue was depleted drastically by more than 50% when compared to the non-cerulein-treated control. The oral administration of dihydro-resveratrol significantly suppressed glutathione depletion in the cerulein-induced pancreata.

The solubility of dihydro-resveratrol in a methanol-based solvent was at least 5 times higher than that of trans-resveratrol. By assessing the mitochondrial metabolic rates of acini, the cytotoxicity of dihydro-resveratrol was shown to be approximately 500 μM whereas that of trans-resveratrol was roughly 250 μM. Thus, the cytotoxicity of dihydro-resveratrol was 50% lower than that of trans-resveratrol.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1),

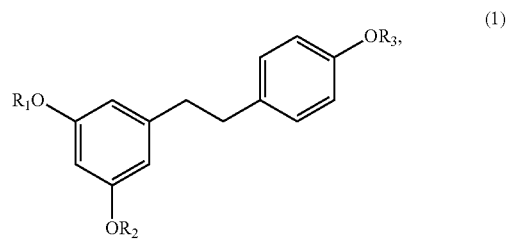

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

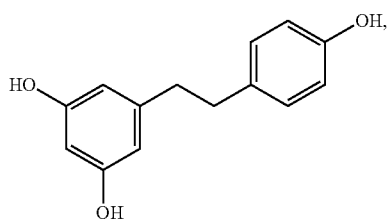

and the derivatives or chemical variants thereof; or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2),

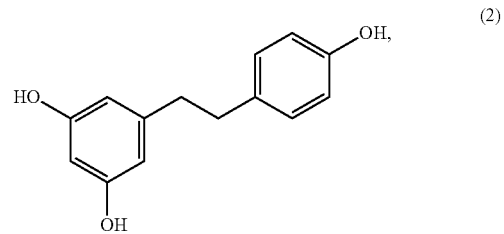 [SMILES: Oc1ccc(CCc2cc(O)cc(O)c2)cc1]

which is a stilbenoid derivative having a chemical name of trans-3,5,4'-trihydroxybibenzyl by hydrogenating of trans-resveratrol.

In a second embodiment of the second aspect of the present invention there is provided a method of preparing the compound of molecular formula $C_{14}H_{14}O_3$ and of formula (2) wherein the hydrogenating of trans-resveratrol comprises steps of stirring a solution of trans-resveratrol in anhydrous EtOH at room temperature under 5 atm $H_2$ pressure in the presence of 10% Pd/C for 8 hours;
filtering off the catalyst from the stirred solution;
evaporating the filtrate in vacuum to produce a residue;
eluting the residue using silica gel chromatographic separation with petroleum ether and ethyl acetate (1:1) to produce dihydro-resveratrol.

Further Embodiments of the Present Invention

TGF-□ has been reported by some previous studies as a potent inducer of PSC activation in which a series of fibrotic mediators, including FN1, are being up-regulated. In cultured LTC-14 cells, which are immortalized PSCs from rat, the expression levels of fibrotic filament □-SMA and ECM protein FN1 are remarkably elevated by the exogenous addition of recombinant TGF-□ (5 ng/mL). In one further embodiment of the present invention, the inventors discover that the administration of dihydro-resveratrol significantly attenuate the expression levels of □-SMA and FN1 in rat PSCs upon the challenge of TGF-□. The derivatives of dihydro-resveratrol exert similar suppressive effect in PSCs. When compared to the renowned anti-oxidant trans-resveratrol, the inhibitory effect of dihydro-resveratrol is more significant. Among the testing stilbenoids, dihydro-resveratrol exerts the most potent anti-fibrotic effect in PSCs despite they possess modest structural differences.

The present invention provides a compound for suppressing a fibrotic mediator of stellate cells present in an internal organ of a subject in need with a formula of

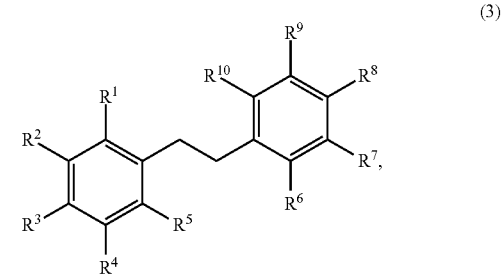

wherein $R^2$ and $R^4$ are each independently selected from —$OR^{11}$ and —$OC(O)R^{11}$;

$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof;

or a mixture of said compound, the derivative and/or chemical variants thereof.

The present invention further provides nine embodiments of compounds for suppressing a fibrotic mediator of stellate cells present in an internal organ of a subject in need with formula of:

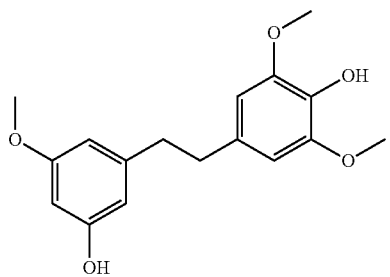

(i)

4-[2-(3-Hydroxy-5-methoxyphenyl)ethyl]-2,6-dimethoxy-phenol

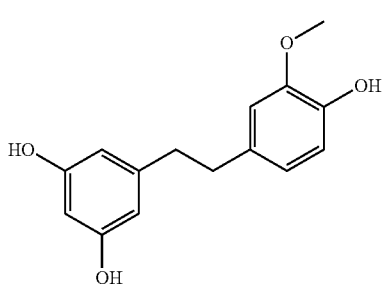

(ii)

Tristin

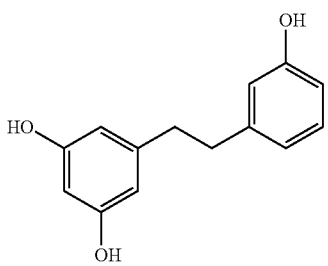

(iii)

3,3',5-Trihydroxydibenzyl

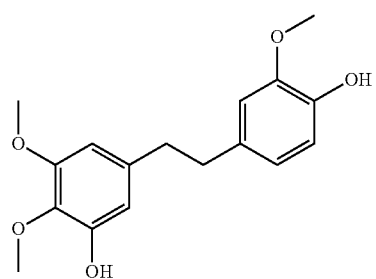

(iv)

5-[2-(4-Hydroxy-3-methoxyphenyl)ethyl]-2,3-dimethoxy-phenol

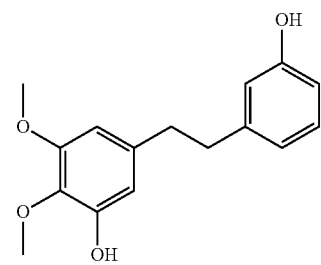

(v)

5-[2-(3-Hydroxyphenyl)ethyl]-2,3-dimethoxy-phenol

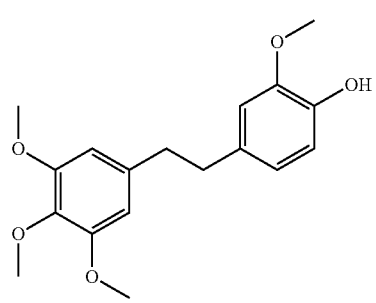

(vi)

Crepidatin

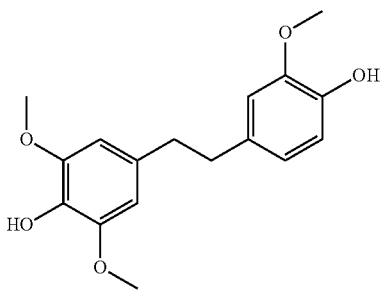

(vii)

Moscatilin

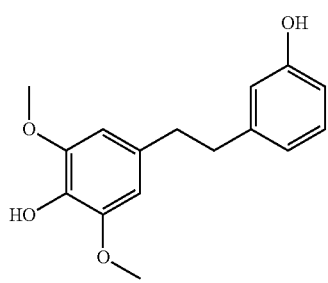

(viii)

Aloifol I

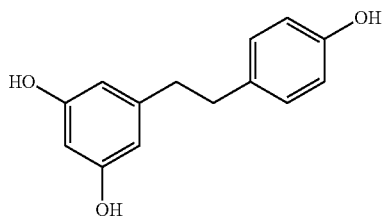

(2)

dihydro-resveratrol

The internal organ can be, for example, pancreas, liver, kidney and lung of a subject. The subject can be a human subject.

Experiments:

LTC-14 cells were cultured at 37° C. under a humidified condition of 95% air and 5% $CO_2$ in IMDM supplemented with 10% fetal bovine serum (FBS). Cells used in all the experiment were among passages 9 to 25. LTC-14 cells were seeded at a density of $1\times10^5$/well in a 12-well plate, and incubated with recombinant TGF-☐ at 5 ng/mL with dihydro-resveratrol at 0, 1, 5, 10 and 20 µg/mL in IMDM supplemented with 0.2% FBS for 24 hours. Cells were then harvested for protein extraction and Western blotting analysis or immunofluorescent staining.

Total proteins of the LTC-14 cells are extracted using RIPA lysis buffers containing protease inhibitors. Cell lysates were loaded and separated by SDS-polyacrylaminde gel electrophoresis. After wet electroblotting, proteins were transferred onto PVDF membranes (Bio-rad), blocked with 5% non-fat milk, probed with antibodies and visualized by utilization of an ECL kit (GE Healthcare).

For immunofluorescent staining of ☐-SMA, LTC-14 cells were seeded at a density of $1\times10^5$ onto the poly-L-lysine-coated cover slips in a 24-well plate, incubated with TGF-☐ at 5 ng/mL with dihydro-resveratrol at 0, and 10 µg/mL in IMDM supplemented with 0.2% FBS for 24 hours. Cells were then fixed, blocked with 3% BSA, probed with antibodies and mounted with fluorescence mounting medium containing 4', 6-diamidino-2-phenylindole (DAPI). Images were captured using the Nikon microscope and analyzed by the SPOT advanced software.

Evaluation of biological activities. C57/BL6 mice aged 28 days weighing in the range of 20 to 25 g were randomly assigned into 4 groups of 6 to 8 individuals. The mice were housed with an ambient temperature of 23±2° C., a relative humidity of 60 to 80% and a 12-h light/dark cycle. Prior to the glucose tolerance test, the mice were starved overnight but allowed with free access to water. Experimental chronic pancreatitis was induced in the mice by four hourly i.p. injections of cerulein at the supramaximally stimulating dose (50 µg/kg) a day, 3 days a week, in a total of 6 weeks. The control group received injections of 0.9% saline instead of cerulein in the same volume and at same time intervals. The treatment groups given with cerulein and oral doses of dihydro-resveratrol (20 mg/kg/day) were designated as Cer+D-res. A dosage of dihydro-resveratrol at 50 mg/kg/day had also been attempted in the treatment course, but no statistically significant difference from the dose at 20 mg/kg/day in fibrosis formation was achieved. Nevertheless, no adverse effect was obtained from this higher dosage in the in vivo trial. Thus, it concludes that an effective dosage of dihydro-resveratrol is at least 20 mg/kg/day. The group given with trans-resveratrol was designated as Cer+Res. The drug intervention of both compounds was given from the first day of week 4 till the end of experiment, i.e. in a total of 3 weeks. At the end of the 6-week experiment, mice were subjected to the intraperitoneal glucose tolerance test (IPGTT). Mice had been starved for 14 hours prior to the IPGTT, in which a 15% (w/v) glucose solution was injected to individual animals at 1.5 g glucose per kg body weight. About 1 µL of blood will be obtained from the tail vein, and blood glucose levels were monitored 30 min before (i.e. fasting level) and 10, 20, 30 and 60 min after glucose injection using a glucometer (Medisign, Korea). Upon scarification, pancreases were immediately removed, weighed, trimmed from fat and fixed in 4% paraformaldehyde-phosphate buffered saline overnight at 4° C. Samples were then processed, embedded in paraffin wax, sectioned and subjected to immunostaining.

According to the dose translation formula, human equivalent dosage (mg/kg)=Animal dose (mg/kg) multiplied by animal Km/human Km, where mouse Km is 3 and human Km is 37 (*Guidance for Industry Estimating the Maximum Safe Starting Dose in Initial Clinical Trials for Therapeutics in Adult Healthy Volunteers*), the effective human equivalent dosage of dihydro-resveratrol of the present invention is at least 1.622 mg/kg/day.

In yet another embodiment of the present invention, 8 other derivatives (compounds i to viii) of dihydro-resveratrol and dihydro-resveratrol (compound 2) are shown in FIGS. 8A-8I. In this embodiment, each compound is experimented accordingly as follows:

Experiment with the Embodiments of Compounds in FIGS. 8A-8I

LTC-14 cells were pre-incubated with TGF-] (5 ng/mL), and treated with trans-resveratrol (Resv) or dihydro-resveratrol (D-Res) or stilbene compounds i-viii at 20 µg/mL for 24 hours. Control was not treated with Resv or any stilbenoids. Total proteins were extracted and analyzed using Western blotting. This is shown in FIG. 9.

LTC-14 cells are pancreatic stellate cells. α-SMA is the hallmark component of fibrogenesis whereas β-actin serves as a loading control. Thus, the expression level of α-SMA implies the degree of PSC activation. TGF-β was added since it is regarded as a potent inducer of fibrotic events. Suppressive effect on α-SMA expression level is tested among dihydro-resveratrol and compounds i to viii in relation to trans-resveratrol (Resv). All of the testing compounds exert suppressive effect of α-SMA expression level.

LTC-14 cells were pre-incubated with TGF-□ (5 ng/mL), and treated with trans-resveratrol or dihydro-resveratrol at the indicated concentrations. Total proteins were extracted and analyzed using Western blotting. This is shown in FIG. 10.

FN1 is a major extracellular matrix protein produced during fibrogenesis or upon the activation of pancreatic stellate cells. Its expression level implies the degree of fibrogenesis. Suppressive effect on levels of FN1 and α-SMA is tested between dihydro-resveratrol (i.e. compound 2) and trans-resveratrol.

LTC-14 cells were pre-incubated with TGF-□ (5 ng/mL), and treated with dihydro-resveratrol at 20 µg/mL for 24 hours prior to immunofluorescent staining.

LTC-14 cells are pancreatic stellate cells. α-SMA is the hallmark component of fibrogenesis whereas β-actin serves as a loading control. Thus, the green fluorescent signal (identified by arrow marks in FIG. 11) of α-SMA implies the degree of PSC activation. TGF-β was added since it is regarded as a potent inducer of fibrotic events. Suppressive effect of dihydro-resveratrol on α-SMA expression level is tested.

Pancreatic tissue sections are stained with antibody against FN1; thus, the immunostaining signals imply the degree of FN1 deposition in the parenchyma. The treatment with dihydro-resveratrol at 20 mg/kg/day (Cer+D-Res) reduces such deposition in chronic pancreatitis in a manner more significant to trans-resveratrol (Cer+Res). This is shown in FIG. 12.

Evaluation of biological activities. C57/BL6 mice aged 28 days weighing in the range of 20 to 25 g were randomly assigned into 4 groups of 6 to 8 individuals. The mice were housed with an ambient temperature of 23±2° C., a relative humidity of 60 to 80% and a 12-h light/dark cycle. When oral administration of dihydro-resveratrol (20 mg/kg/day) is given, the fasting blood glucose levels of the chronic pancreatitis mice (Cer) become markedly higher than those of the control group, indicating these chronic pancreatitis mice develop hyperglycemia, a discernible feature of diabetes. Importantly, their impaired glucose tolerance has been significantly rectified by the 3-week dihydro-resveratrol treatment (Cer+D-Res). As a result, the hyperglycemic condition of the chronic pancreatitis mice is improved. This is shown in FIG. 13.

When oral administration of dihydro-resveratrol (Cer+D-Res) is given at 20 mg/kg/day, the severity of pancreatitis and the shrinkage and destruction of islets, explicitly beta cells, are notably ameliorated. As shown in FIG. 14, the pancreatic beta-cell area is reflected by the immunofluorescent insulin signals. A reduced beta-cell area or mass implicates the deficiency in glucose tolerance, or the development of diabetes. Thus, the restoration of beta-cell area by the dihydro-resveratrol treatment indicates this stilbenoid is beneficial to the treatment of pancreatogenic diabetes (i.e. Type3c DM).

According to the dose translation formula, human equivalent dosage (mg/kg)=Animal dose (mg/kg) multiplied by animal Km/human Km, where mouse Km is 3 and human Km is 37 (*Guidance for Industry Estimating the Maximum Safe Starting Dose in Initial Clinical Trials for Therapeutics in Adult Healthy Volunteers*), the effective human equivalent dosage of dihydro-resveratrol of the present invention is at least 1.622 mg/kg/day.

Another Further Embodiments of the Present Inventions

*Dendrobium* plants, commonly called "Shi Hu", are widely used in the traditional Chinese medicine (TCM) system as well as in folk medicines for treating various kinds of diseases, such as chronic atrophic gastritis, diabetes and cardiovascular disease. *Dendrobium*-derived extracts or ingredients contain substantial amounts of various stilbenoids, such as trans-resveratrol and dihydro-resveratrol, which are potential compounds for combating oxidative stress in the human body. However, the uses of these compounds for skin-protection or skin whitening have not been disclosed.

As oriental cosmetics prefer plant-based composition, the present invention relates to the use of *Dendrobium*-derived stilbenoids, particularly trans-resveratrol, dihydro-resveratrol or dihydro-resveratrol derivatives in reducing melanin formation with a potential to inhibit the generation of oxidative radicals and ROS. The present composition is applied to the subject in need thereof via topical administration. The present composition is in the form of a day cream, a night cream, a face lotion, a body lotion, a body butter, a skin peel, a mask, a shower gel, a sun cream, a sun lotion, an after sun cream or an after sun lotion.

The present composition comprises one or more extract(s) derived from *Dendrobium* plants.

The present composition comprises one or more stilbenoids with the following formula:

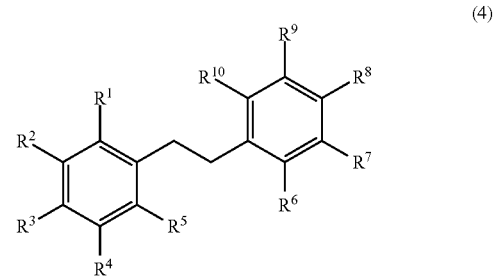
(4)

wherein $R^2$, $R^4$, and $R^8$ are each independently selected from —$OR^{11}$, —$OCH_2R^{12}$, —$OC(O)R^{11}$, —$OCH_2C(O)OR^{12}$ and —$OC(O)CH_2R^{12}$;

$R^1$, $R^3$, $R^5$, $R^6$, $R^7$, $R^9$ and $R^{10}$ are each independently selected from hydrogen, halogen, trifluoromethyl, $OR^{12}$ and —$OC(O) R^{12}$; or $R^2$ and $R^3$, or $R^7$ and $R^8$ may be taken together with the carbon atoms to which they are attached to form a cyclic group;

$R^{11}$ is independently selected from —$(CH_2)$-hydrocarbyl, $C_{2-10}$ alkyl, alkenyl and heterocyclyl, Each of these groups is optionally substituted with 1, 2, 3, 4 or 5 $R^{13}$;

$R^{12}$ is independently selected from hydrocarbyl and heterocyclyl, either of which is optionally substituted with 1, 2, 3, 4 or 5 $R^{13}$;

$R^{13}$ is independently selected from halogen, trifluoromethyl, cyano, nitro, oxo, —$OR^{14}$, —$C(O)R^{15}$, —$C(O)$ $N(R^{14})R^{15}$, —C(O)O$R^{14}$, —OC(O)$R^{15}$, —S(O)$_2$$R^{14}$, —S(O)$_2$N($R^{14}$)$R^{15}$, —N($R^{14}$)$R^{15}$;

$R^{14}$ and $R^{15}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof.

The present composition comprises stilbenoid(s) with the following formula:

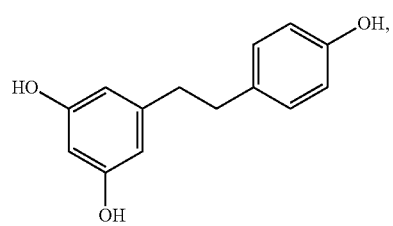 [SMILES: Oc1ccc(CCc2cc(O)cc(O)c2)cc1]

which is dihydro-resveratrol, and the derivatives or chemical variants thereof; or a mixture of said compound, the derivative and/or chemical variants thereof, or with a formula of:

DR1

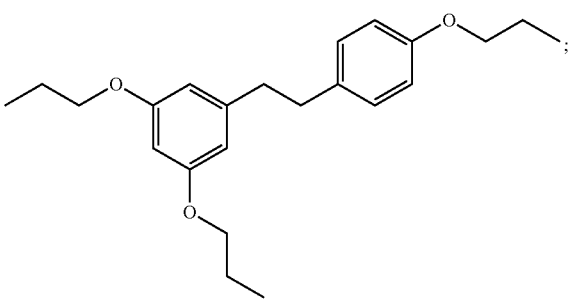

DR2

DR3

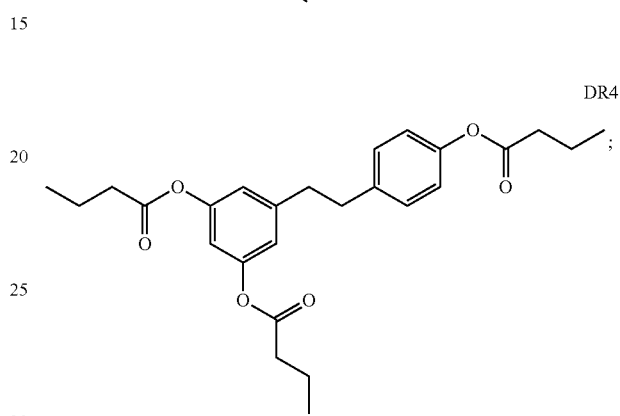

DR3

DR4

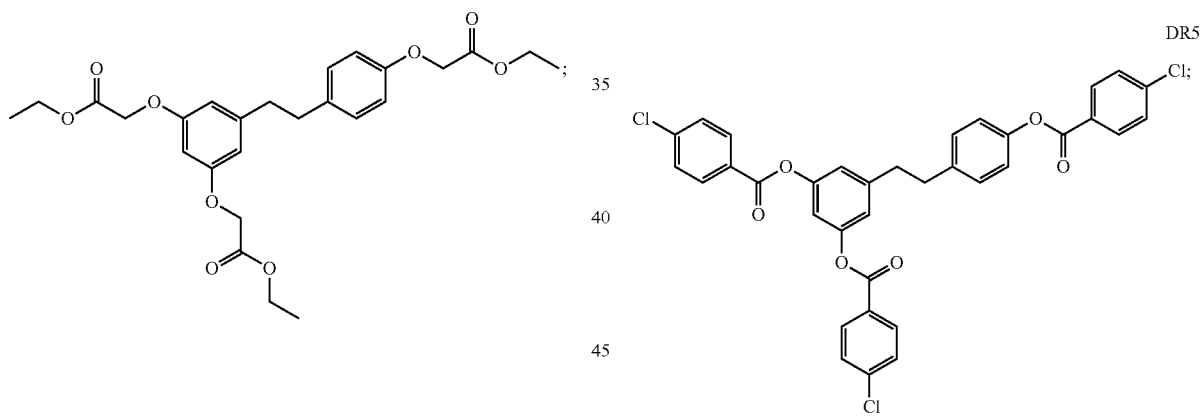

DR5

DR6

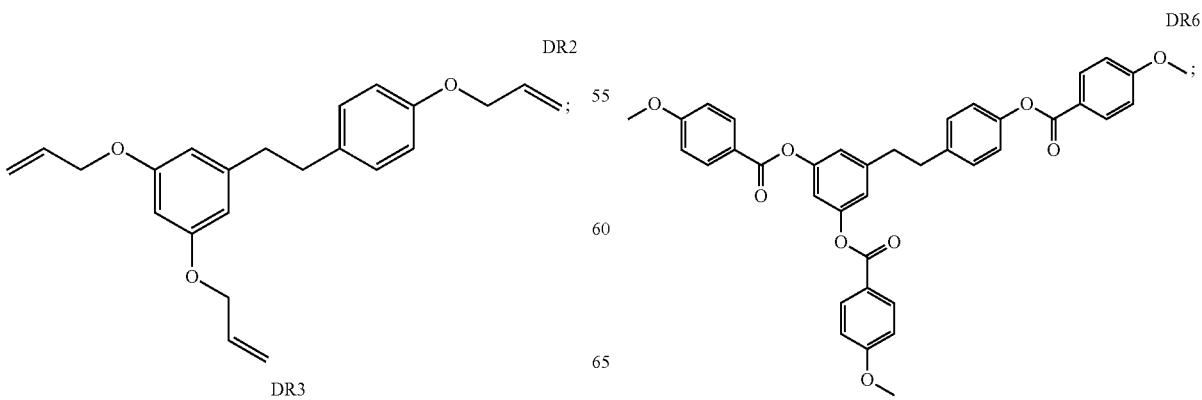

DR7
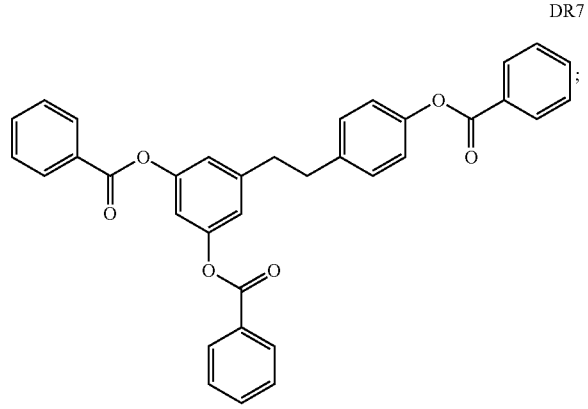 [SMILES: O=C(Oc1ccc(CCc2cc(OC(=O)c3ccccc3)cc(OC(=O)c3ccccc3)c2)cc1)c1ccccc1]

DR8
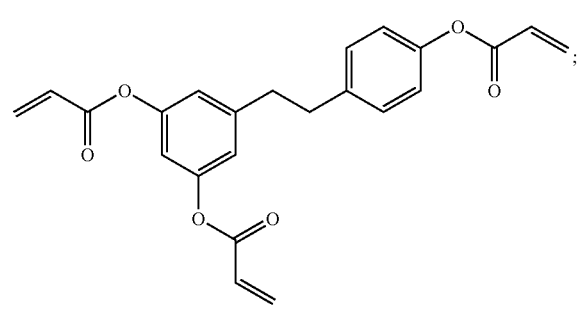

DR9
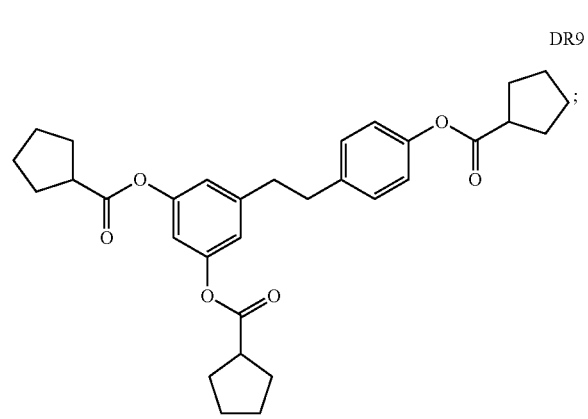 [SMILES: O=C(Oc1ccc(CCc2cc(OC(=O)C3CCCC3)cc(OC(=O)C3CCCC3)c2)cc1)C1CCCC1]

DR10
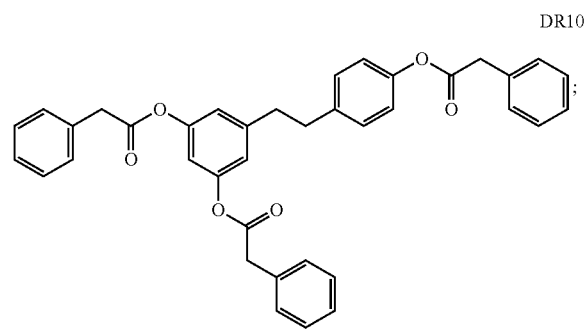

DR11
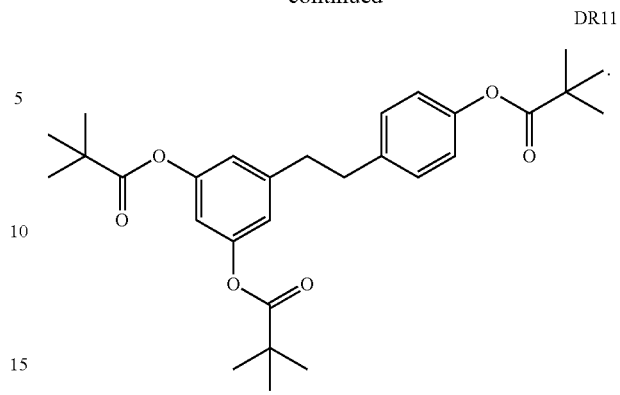

The present composition for skin whitening and skin protection comprises stilbenoid(s) with the following formula:

(5)

wherein
$R^2$, $R^4$, and $R^8$ are each independently selected from —$OR^{11}$, —$OCH_2R^{11}$, —$OC(O)R^{11}$, —$OCH_2C(O)OR^{11}$ and —$OC(O)CH_2R^{11}$;

$R^1$, $R^3$, $R^5$, $R^6$, $R^7$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, $C(O)OR^{13}$, —$OC(O)R^{14}$, —$S(O)_2R^{13}$, —$S(O)_2N(R^{13})R^{14}$, $N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof.

To determine the antioxidant capacity, a spectrophotometric decolorization assay complemented with pre-formed radical monocation of 2,2'-azinobis-(3-ethylbenzothiazoline-6-sulfonic acid), also known as ABTS, is used. In this assay, ABTS (Abcam, USA) is dissolved in water to a 7 mM concentration and ABTS radical cation is produced by reacting the ABTS stock solution with 2.45 mM ammonium persulfate (Sigma-Aldrich, USA) and allowing the mixture to stand in the dark at room temperature for 16 hours before use. When testing the *Dendrobium* extract samples or stilbenoid samples, the ABTS radical solution is diluted with ethanol to an absorbance of 0.70 at 734 nm and equilibrated at 30° C. The dilutions of testing samples (0.1 mL) or DMSO (0.1 mL) are incubated with ABTS radical solution (0.9 mL) for 15 min prior to the absorbance taking at 734 nm. DMSO is served as a vehicle treatment whereas Trolox (Abcam, USA), a renowned derivative vitamin E, ranging from 0.001 to 0.05 mg/mL is used as a positive drug reference. The antioxidant capacity of testing samples is expressed as the amount equivalent to Trolox in milligrams (mg) according to the Trolox standard curve.

Upon the incubation with dihydro-resveratrol (D-Res), trans-resveratrol (Res), *Dendrobium* extract samples or other stilbenoid samples (compounds DR1 to DR11), the pre-formed ABTS radicals have been scavenged, and their antioxidant capacity is normalized to the Trolox positive standards as illustrated in Table 3.

TABLE 3

Antioxidant capacity of stilbenoids equivalent to amount of Trolox (mg)

| Compound | Trolox equivalent (mg) | Standard deviation |
| --- | --- | --- |
| D-Res | 4969.611 | 333.841 |
| Res | 4296.325 | 83.132 |
| DR1 | 105.736 | 24.978 |
| DR2 | 30.178 | 52.270 |
| DR3 | 119.325 | 90.071 |
| DR4 | 94.277 | 84.519 |
| DR5 | 0 | 0 |
| DR6 | 0 | 0 |
| DR7 | 0 | 0 |
| DR8 | 15.893 | 27.527 |
| DR9 | 0 | 0 |
| DR10 | 0 | 0 |
| DR11 | 0 | 0 |

The cellular melanin content and tyrosinase activity are determined in cultured B16 and A375 melanocytes. In fact, melanocytes are melanin-producing cells whereas melanin refers to groups of endogenous pigments that give multitude of skin colors. B16 cells (Shanghai Institutes for Biological Science, Chinese Academy of Sciences, China) and A375 cells (American Type Culture Collection, USA) are routinely grown in DMEM medium (Gibco, USA) supplemented with 10% heat-activated fetal bovine serum (FBS, Gibco, USA) and 1% penicillin/streptomycin (Gibco, USA) in a humidified atmosphere of 95% air and 5% $CO_2$ at 37° C.

To determine the cellular melanin content, melanocytes are seeded in 12-well plates ($8 \times 10^4$ cells/well) and stimulated with alpha-melanocyte-stimulating hormone ($\alpha$-MSH, 100 nM) for 24 hours. Such stimulation is aimed to accelerate the cellular formation of melanin in the melanocytes, so that the reducing ability of the testing compounds or extracts on melanin formation becomes more apparent. Followed by the $\alpha$-MSH stimulation, cells are then treated with different *Dendrobium* extract samples or stilbenoid samples (5 µL) or DMSO (5 µL, Sigma-Aldrich, USA) for another 24 hours. DMSO serves as a vehicle treatment. At the end of experiment, cells are trypsinized for detaching from the culturing plates. After centrifugation, the melanin pellet of each sample is incubated with 100 µL of 1 N Sodium hydroxide solution (Sigma-Aldrich. USA) for 1.5 hours at 70° C. After cooling to room temperature, the solution is centrifuged at 15,000×g for 10 min. The supernatant (100 µL) of each sample is transferred to 96-well plates for a reading of absorbance taken at 405 nm. Relative melanin content of each sample is normalized with its protein content and presented as the percentage change over the DMSO-treated cells.

Upon the incubation with dihydro-resveratrol (D-Res), trans-resveratrol (Res), *Dendrobium* extract samples or other stilbenoid samples (compounds DR1 to DR11), the cellular melanin contents in B16 and A375 melanocytes have been reduced as illustrated in FIGS. 15 to 17.

To determine the cellular tyrosinase activity, melanocytes are seeded in 12-well plates ($8 \times 10^4$ cells/well) and stimulated with $\alpha$-MSH (100 nM) for 24 hours. Post the $\alpha$-MSH stimulation, cells are treated with different testing samples (5 µL) or DMSO (5 µL) for another 24 hours. At the end of experiment, the cells are washed with ice-cold phosphate buffer saline (PBS, pH 6.8) (Gibco, USA) twice and then lysed with 150 µL of PBS (pH 6.8) containing 0.1% Triton X-100 on ice. The cell lysates are centrifuged at 15,000×g for 15 min at 4° C. An aliquot of 50 µL supernatant is mixed with 50 µL L-3,4-dihydroxyphenylalanine (L-DOPA, Abeam, USA) solution (0.2% in PBS, ph 6.8) in 96-well plates and incubated at 37° C. for 2 hours under darkness. Optical density of each sample is measured at 475 nm. The absorbance is normalized with the protein content of each sample. The relative activity of cellular tyrosinase in melanocytes is calculated and presented as the percentage change over the DMSO-treated cells. In addition, another set of experiment is collected for Western blotting analysis of the expression levels of TRP1 and TRP2, so as their upstream regulators p-AKT and p-38.

Upon the incubation with dihydro-resveratrol (D-Res), trans-resveratrol (Res), *Dendrobium* extract samples or other stilbenoid samples (compounds DR1 to DR11), the tyrosinase activity in B16 and A375 melanocytes has been inhibited as illustrated in FIGS. 18 to 20. Western blotting results are shown in FIG. 21.

To determine the generation of intracellular ROS in melanocytes, B16 or A375 cells are seeded in 12-well plates ($8 \times 10^4$ cells/well) and stimulated with $\alpha$-MSH (100 nM) for 24 hours. At the end of $\alpha$-MSH incubation, cells are trypsinized for detaching from the culturing plates and subjected to cellular ROS detection assay (Abeam) according to manufacturer's instruction. In brief, cells are stained with 20 µM DCFDA for 30 min at 37° C. After staining, cells are treated with tert-butyl hydrogen peroxide (TBHP, 55 nM) for an evident level of ROS elevation prior to a 4-hour incubation with our testing extracts or compounds or ascorbic acid (AC) in a volume of 5 µL. Signals of ROS generation will be detected using a fluorescence microplate reader. DCF are excited by the 488 nm laser. Results of this assay are presented in FIG. 22.

All assays are performed in triplicate and repeated for at least 3 times in individual experiments. The results are presented as the mean±standard deviation. Variance between two groups is evaluated by Student's t-test whereas variance among more than two groups is calculated by means of one-way analysis of variance (one-way ANOVA). A p value of less than 0.05 is considered as statistically significant.

To determine the skin color of the individual human subjects, the initial skin conditions at the arms of the individuals are tested by the skin colorimeter MPA 5 on day 0. The individual typology angle (ITA°) is calculated by the colorimeter based on the luminance (L*) and yellow-blue component (b*) values. The greater the ITA° value, the greater the skin whiteness [S. Del Bino and F. Bernerd. Variations in skin colour and the biological consequences of ultraviolet radiation exposure. *British Journal of Dermatology* 2013; 169 (Suppl. 3), 33-40]. In fact, skin colors are classified into 6 major divisions: very light, light, intermediate, tan, brown and dark as listed in Table 4. Two areas (2 cm×2 cm each) are selected as treated areas whereas regions surrounding the treated areas on the arms are regarded as control areas. A volume of 200 µL of the testing stilbenoids (2% by weight dissolved in ethanol) is applied to the designated area twice a day, day and night. At the end of the first week (day 7), individuals are tested with the skin colorimeter for recording the data about using the stilbenoids for 7 days. Again, at the end of the second week (day 14), individuals are tested with the skin colorimeter for recording the data about using the stilbenoids for 14 days. The ITA° readings are presented in Table 5. Overt whitening effect from dihydro-resveratrol or trans-resveratrol is obtained from most individuals. A set of representative images taken from a human individual who uses the topical treatment is shown in FIG. 23.

TABLE 4

Skin classification based on ITA°

| Individual typology angle (ITA°) | Skin classification |
| --- | --- |
| ITA° > 55° | Very light |
| 41° < ITA° < 55° | Light |
| 28° < ITA° < 41° | Intermediate |
| 10° < ITA° < 28° | Tan |
| −30° < ITA° < 10° | Brown |
| ITA° < −30° | Dark |

TABLE 5

ITA° measurements of individual human subjects on the indicated time-points

| Individual | day 0 nil | day 7 | | | day 14 | | |
| --- | --- | --- | --- | --- | --- | --- | --- |
| | | 2% D-Res | 2% Res | nil | 2% D-Res | 2% Res | nil |
| No. 1 | 46.3 ± 3.525 | 49.0 ± 1.732 | 47.7 ± 1.155 | 40.3 ± 2.517 | 52.4 ± 1.166 | 46.4 ± 0.548 | 41.8 ± 0.860 |
| No. 2 | 46.3 ± 0.473 | 41.1 ± 3.391 | 39.2 ± 2.564 | 36.4 ± 3.530 | 49.8 ± 4.630 | 44.8 ± 2.871 | 39.6 ± 2.542 |
| No. 3 | 41.1 ± 2.895 | 35.0 ± 1.000 | 38.0 ± 1.732 | 41.4 ± 2.782 | 33.8 ± 0.837 | 36.2 ± 1.789 | 38.8 ± 1.855 |
| No. 4 | 34.2 ± 1.779 | 26.8 ± 2.371 | 22.4 ± 1.715 | 26.8 ± 1.789 | 35.2 ± 2.103 | 29.4 ± 1.342 | 29.0 ± 3.768 |
| No. 5 | 31.2 ± 0.884 | 25.6 ± 1.817 | 26.6 ± 1.159 | 27.0 ± 2.827 | 27.8 ± 1.934 | 34.0 ± 2.168 | 28.2 ± 3.693 |
| No. 6 | 26.8 ± 3.609 | 26.4 ± 2.649 | 28.2 ± 2.718 | 29.4 ± 1.949 | 34.6 ± 0.927 | 41.8 ± 3.372 | 32.6 ± 2.315 |
| No. 7 | 20.8 ± 4.560 | 21.2 ± 0.837 | 20.6 ± 1.140 | 19.8 ± 1.893 | 23.8 ± 2.634 | 20.4 ± 0.578 | 21.6 ± 1.435 |
| No. 8 | 11.5 ± 2.619 | 14.0 ± 2.345 | 14.0 ± 1.232 | 9.0 ± 1.414 | 16.2 ± 1.483 | 9.6 ± 1.342 | 11.2 ± 1.241 |
| No. 9 | −11.3 ± 3.726 | −5.2 ± 0.837 | −7.2 ± 1.789 | −12.0 ± 1.225 | −2.2 ± 0.447 | −7.4 ± 1.140 | −6.2 ± 2.223 |

General Synthetic Route of DR1 to DR3

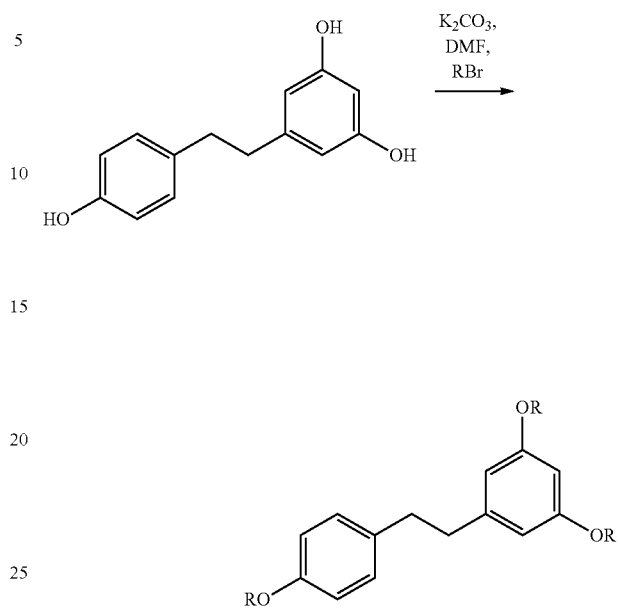

To a mixture of dihydro-resveratrol (0.2 mmol) and RBr (1.2 mmol) in dimethylformamide (DMF, 2 mL), $K_2CO_3$ (1.2 mmol) was added. The resulting mixture was stirred at room temperature until the starting material disappeared on thin-layer chromatography (TLC). The mixture was diluted with $H_2O$ (10 mL) and washed with dichloromethane (DCM, 10 mL) three times. The combined organic layer was washed with saturated sodium chloride (NaCl) twice, dried over anhydrous $Na_2SO_4$, concentrated in vacuum and purified by preparative (prep-)TLC (PE/EA=5/1 or 3/1) to afford the desired compound(s).

DR1

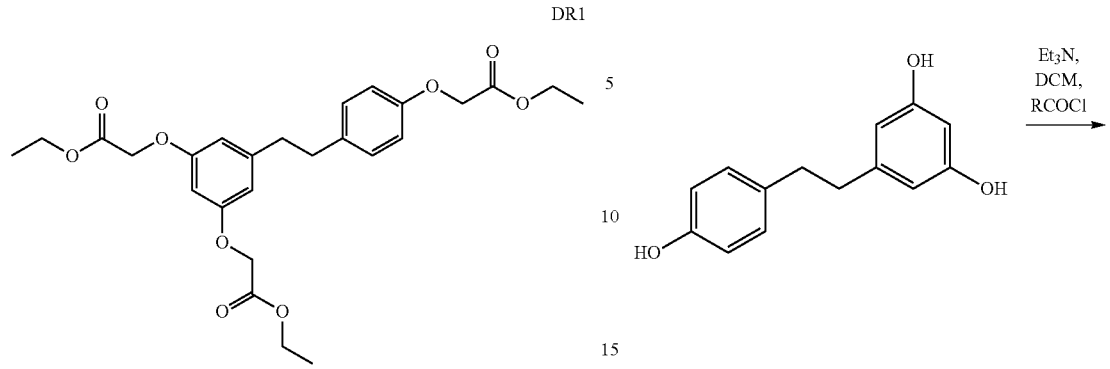

High-resolution mass spectrometry (HRMS): 511.1997 [M+Na]+

Proton nuclear magnetic resonance (¹H NMR, 400 MHz, CDCl₃) δ 1.31 (9H, t, J=7.1 Hz), 2.82 (4H, s), 4.22-4.32 (6H, m), 4.56 (4H, s), 4.60 (2H, s), 6.29-6.41 (3H, m), 6.80-6.86 (2H, m), 7.04-7.13 (2H, m).

DR2

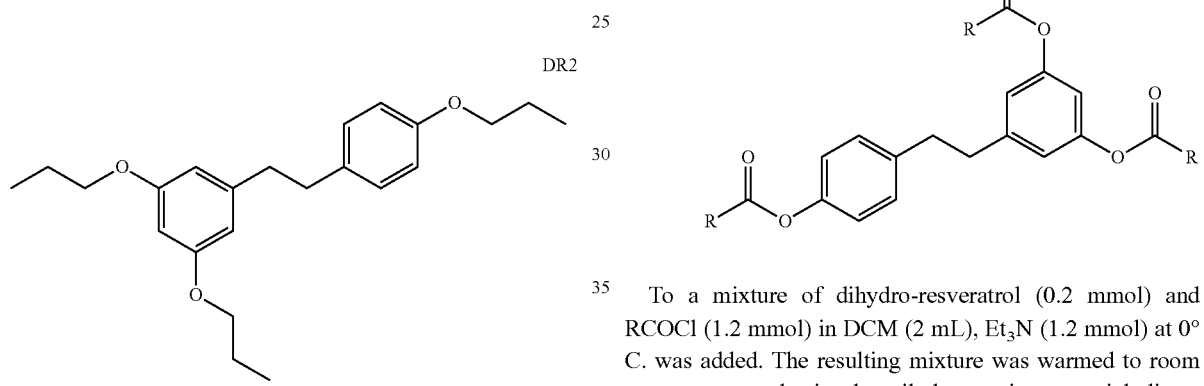

HRMS: 373.1770 [M+Na]+.

¹H NMR (400 MHz, CDCl₃) δ 2.84 (4H, d, J=2.1 Hz), 4.49 (4H, dt, J=5.3, 1.4 Hz), 4.51-4.53 (2H, m), 5.25-5.35 (3H, m), 5.37-5.48 (3H, m), 5.99-6.13 (3H, m), 6.36 (3H, s), 6.81-6.90 (2H, m), 7.05-7.15 (2H, m).

DR3

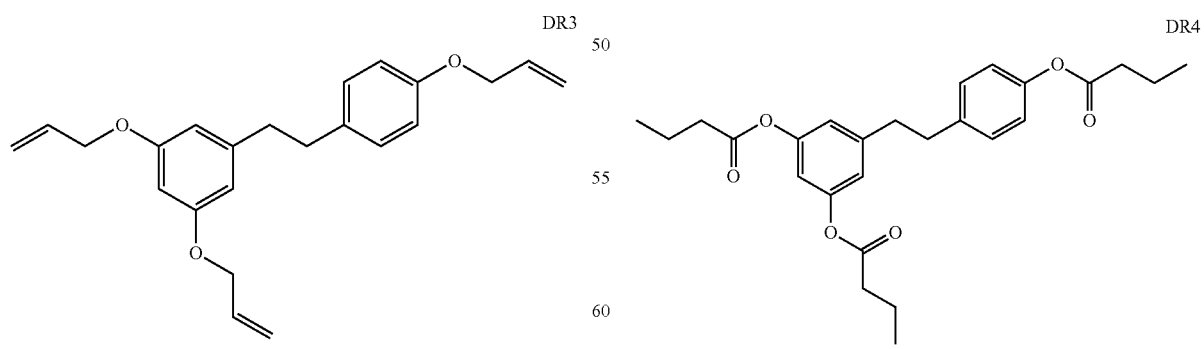

HRMS: 379.2220 [M+Na]+.

¹H NMR (400 MHz, CDCl₃) δ 0.98-1.08 (9H, m), 1.74-1.90 (6H, m), 2.75-2.90 (4H, m), 3.85-3.95 (6H, m), 6.29-6.39 (3H, m), 6.81-6.87 (2H, m), 7.07-7.15 (2H, m).

General Synthetic Route of DR4 to DR11

To a mixture of dihydro-resveratrol (0.2 mmol) and RCOCl (1.2 mmol) in DCM (2 mL), Et₃N (1.2 mmol) at 0° C. was added. The resulting mixture was warmed to room temperature and stirred until the starting material disappeared on TLC. The mixture was diluted with H₂O (10 mL) and washed with DCM (10 mL) three times. The combined organic layer was washed with saturated NaCl twice, dried over anhydrous Na₂SO₄, concentrated in vacuum and purified by prep-TLC (PE/EA=5/1 or 3/1) to afford the desired compound(s).

DR4

HRMS: 463.2044 [M+Na+].

¹H NMR (400 MHz, CDCl₃) δ δ 0.97-1.10 (9H, m), 1.72-1.89 (6H, m), 2.47-2.58 (6H, m), 2.91 (4H, s), 6.74-6.84 (3H, m), 6.94-7.04 (2H, m), 7.13-7.21 (2H, m).

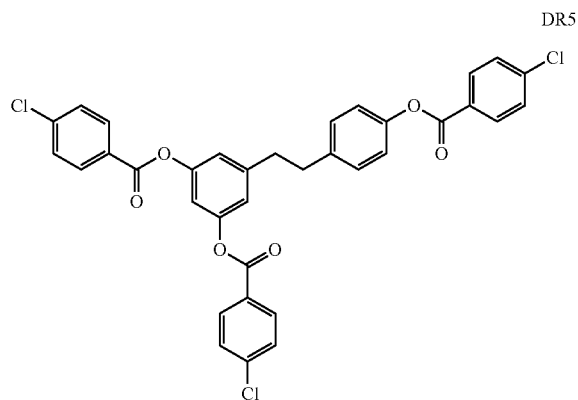
DR5
HRMS: 667.0427 and 669.0408 [M+Na⁺].
¹H NMR (400 MHz, CDCl₃) δ 3.01 (4H, s), 6.99-7.06 (3H, m), 7.10-7.17 (2H, m), 7.22-7.27 (2H, m), 7.46-7.55 (6H, m), 8.09-8.18 (6H, m).
DR6
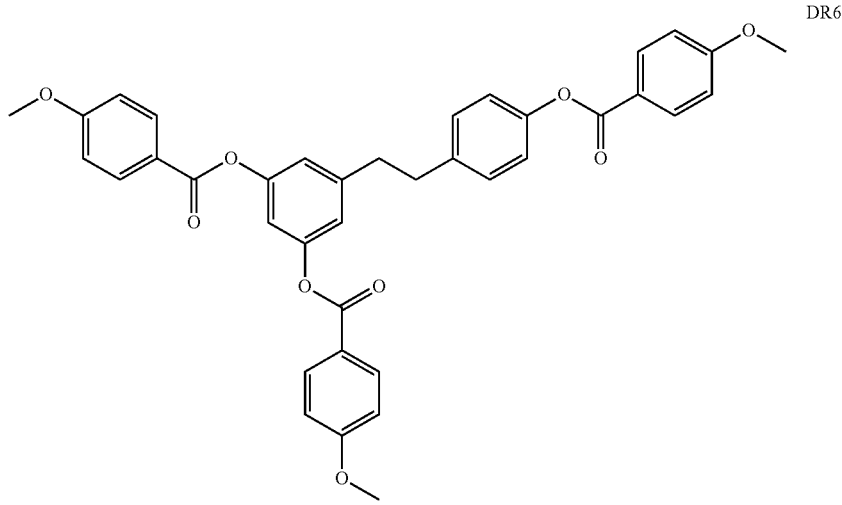
DR6
HRMS: 655.1964 [M+Na⁺].
¹H NMR (400 MHz, CDCl₃) δ 3.00 (4H, s), 3.89-3.92 (9H, m), 6.97-7.04 (9H, m), 7.11-7.16 (2H, m), 7.23-7.27 (2H, m), 8.13-8.18 (6H, m).
DR7
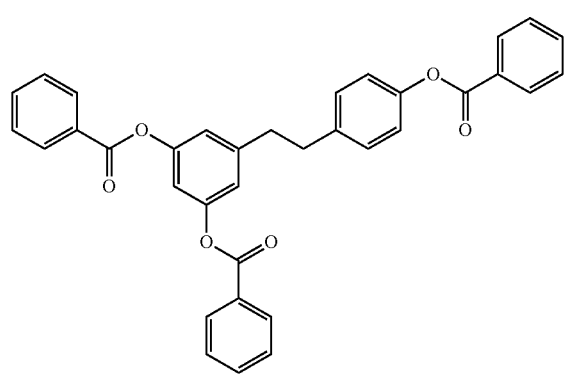
HRMS: 565.1600 [M+Na]+.
¹H NMR (400 MHz, CDCl₃) δ 3.02 (4H, s), 7.02-7.08 (3H, m), 7.12-7.20 (2H, m), 7.25-7.29 (2H, m), 7.50-7.57 (6H, m), 7.60-7.70 (3H, m), 8.17-8.28 (6H, m)
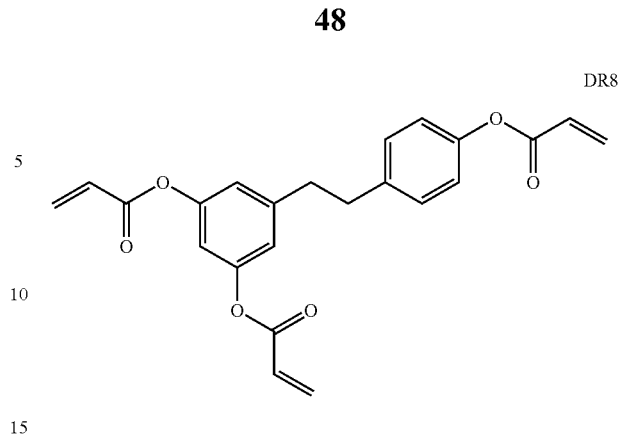
DR8
HRMS: 415.1140 [M+Na]+
¹H NMR (400 MHz, CDCl3) δ 2.94 (4H, s), 5.98-6.08 (3H, m), 6.23-6.43 (3H, m), 6.58-6.70 (3H, m), 6.84-6.97 (3H, m), 7.01-7.13 (2H, m), 7.16-7.26 (2H, m).
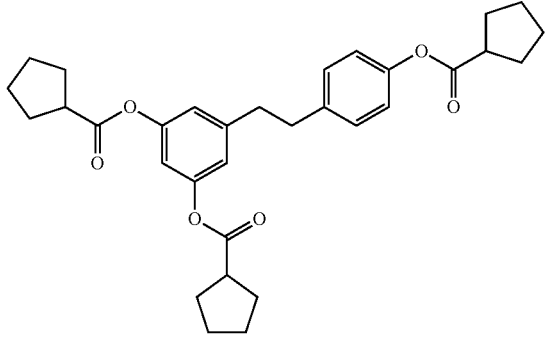
DR9
HRMS: 514.2550 [M+Na]⁺.
¹H NMR (400 MHz, CDCl3) δ 1.61-1.79 (12H, m), 1.88-2.09 (12H, m), 2.82-3.08 (7H, m), 6.72-6.83 (3H, m), 6.96-7.03 (2H, m), 7.15-7.20 (2H, m).

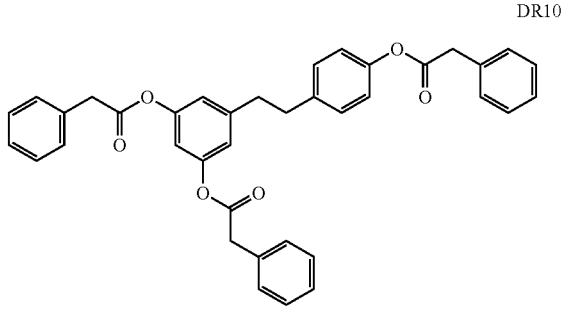 [SMILES: O=C(Cc1ccccc1)Oc1ccc(CCc2cc(OC(=O)Cc3ccccc3)cc(OC(=O)Cc3ccccc3)c2)cc1]

DR10

HRMS: 607.2070 [M+Na]+.

$^1$H NMR (400 MHz, CDCl$_3$) δ 2.91 (4H, s), 5.27 (6H, s), 6.91-6.98 (3H, m), 7.08-7.12 (2H, m), 7.14-7.19 (2H, m), 7.38-7.46 (15H, m).

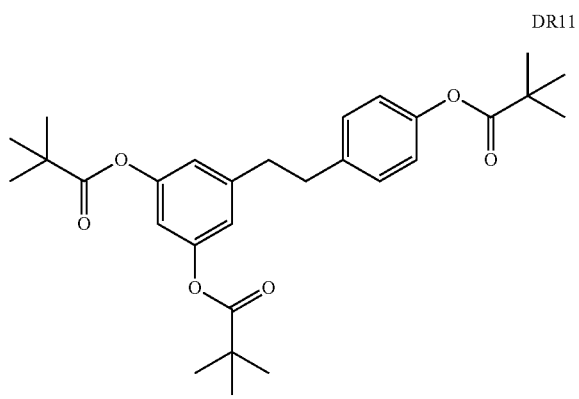 [SMILES: CC(C)(C)C(=O)Oc1ccc(CCc2cc(OC(=O)C(C)(C)C)cc(OC(=O)C(C)(C)C)c2)cc1]

DR11

HRMS: 505.2550 [M+Na]$^+$.

$^1$H NMR (400 MHz, CDCl$_3$) □ 1.34-1.38 (27H, m), 2.86-2.94 (4H, m), 6.77 (3H, d, J=2.1 Hz), 6.93-7.02 (2H, m), 7.14-7.21 (2H, m)

INDUSTRIAL APPLICABILITY

The present invention relates to a skin-protection composition that comprises stilbenoid(s) and/or stilbenoid-containing extract(s) obtained from *Dendrobium* plants, such as *Dendrobium officinale* and *Dendrobium nobile* for the management of melanogenesis, skin-darkening and skin-aging. More particularly, it relates to the usage of *Dendrobium* ingredients and stilbenoids to reduce the formation of melanin in melanocytes. It also relates to the usage of *Dendrobium* ingredients and stilbenoids to reduce the generation of reactive oxygen species and oxidative free radicals. This invention relates to the use *Dendrobium*-derived extracts or ingredients or stilbenoids in the formulation of skin-protection, skin-whitening and/or anti-skin aging products.

The invention claimed is:

1. A compound comprising formula (4):

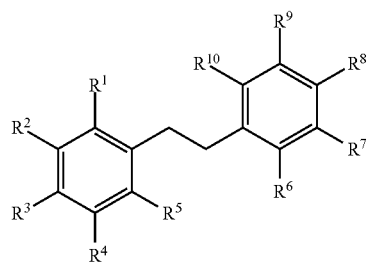

(4)

wherein

R$^2$, R$^4$, and R$^8$ are each independently selected from —OR$^{11}$, —OCH$_2$R$^{12}$, —OC(O)R$^{11}$, —OCH$_2$C(O)OR$^{12}$ and —OC(O)CH$_2$R$^{12}$;

R$^1$, R$^3$, R$^5$, R$^6$, R$^7$, R$^9$ and R$^{10}$ are each independently selected from hydrogen, halogen, trifluoromethyl, —OR$^{12}$ and —OC(O)R$^{12}$; or R$^2$ and R$^3$, or R$^7$ and R$^8$ may be taken together with the carbon atoms to which they are attached to form a cyclic group;

R$^{11}$ is independently selected from —(CH$_2$)-hydrocarbyl, C$_{2-10}$ alkyl, alkenyl, carbocyclyl, aryl and heteroaryl, wherein each of these groups is optionally substituted with 1, 2, 3, 4 or 5 R$^{13}$;

R$^{12}$ is independently selected from hydrocarbyl and heterocyclyl, either of which is optionally substituted with 1, 2, 3, 4 or 5 R$^{13}$;

R$^{13}$ is independently selected from halogen, trifluoromethyl, cyano, nitro, oxo, —OR$^{14}$, —C(O)R$^{15}$, —C(O)N(R$^{14}$)R$^{15}$, —C(O)OR$^{14}$, —OC(O)R$^{15}$, —S(O)$_2$R$^{14}$, —S(O)$_2$N(R$^{14}$)R$^{15}$, —N(R$^{14}$)R$^{15}$;

R$^{14}$ and R$^{15}$ are each independently hydrogen or selected from hydrocarbyl and heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy or a pharmaceutically acceptable salt, prodrug, derivative or chemical variant thereof.

2. A compound selected from DR1, DR2, DR3, DR4, DR5, DR6, DR7, DR8, DR9, DR10 or DR11 with the following formulae respectively:

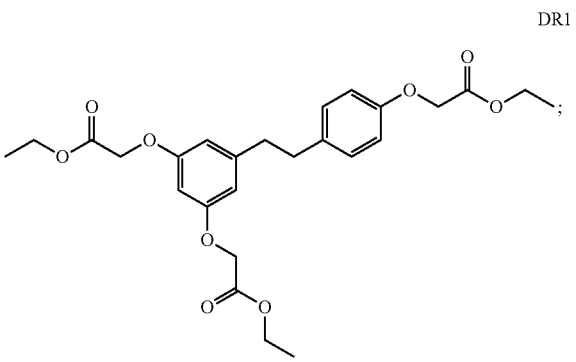

DR1

-continued
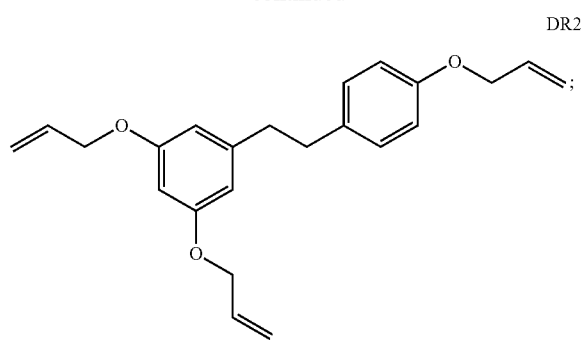
DR2
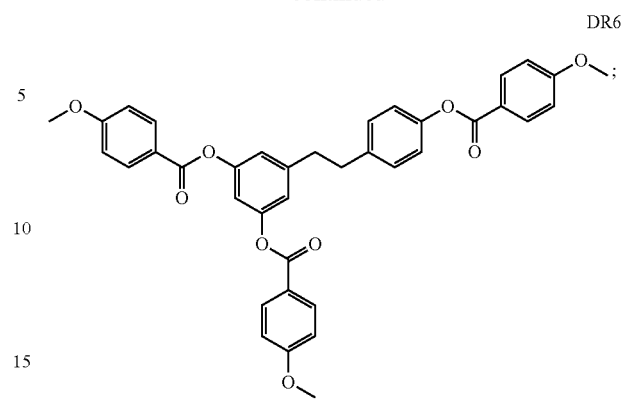
DR6
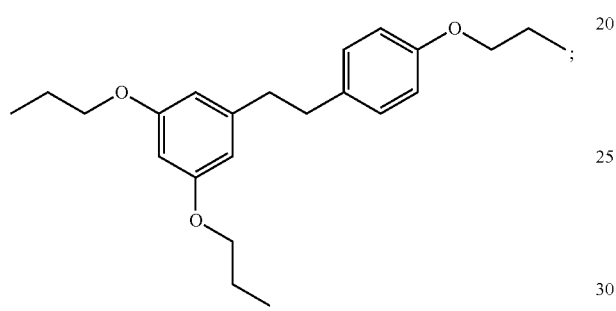
DR3
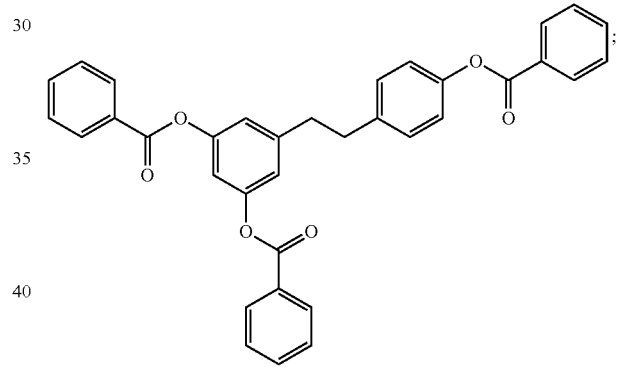
DR7
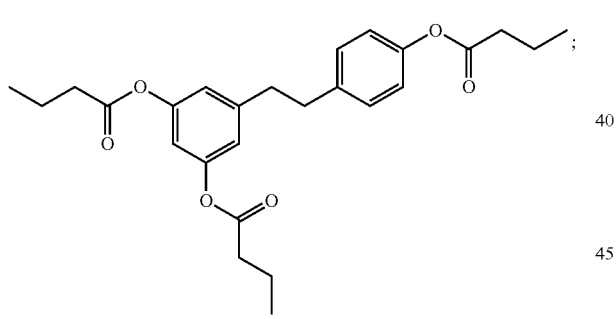
DR4
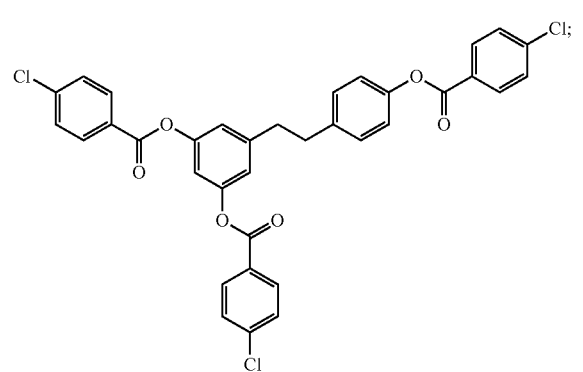
DR5
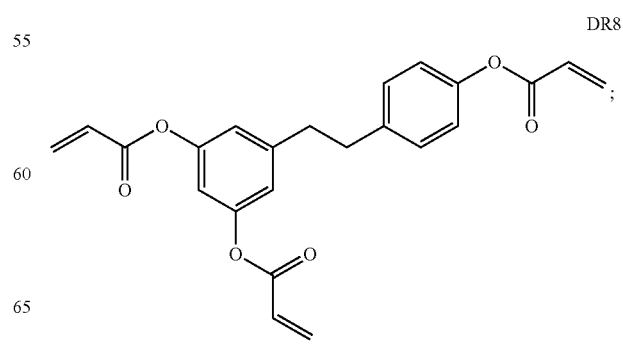
DR8

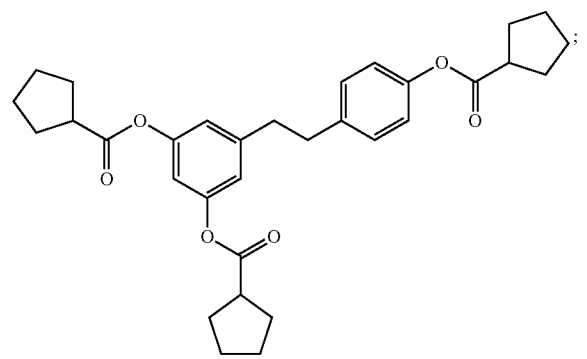
DR9
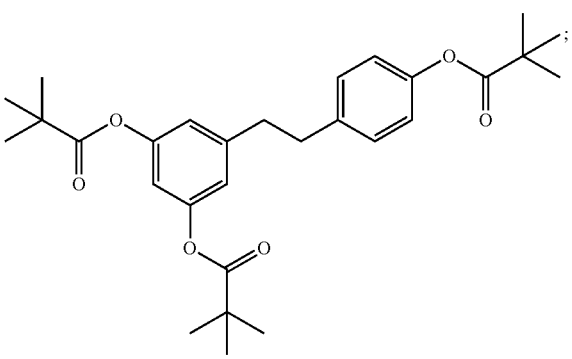
DR11
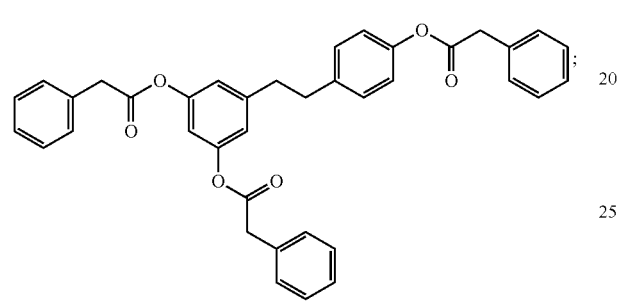
DR10
or a pharmaceutically acceptable salt or prodrug thereof.
3. A pharmaceutical composition comprising the compound of claim 1, wherein the pharmaceutical composition is in the form of a day cream, a night cream, a face lotion, a body lotion, a body butter, a skin peel, a mask, a shower gel, a sun cream, a sun lotion, an after sun cream or an after sun lotion.
* * * * *